(12) United States Patent
Becker et al.

(10) Patent No.: US 6,287,832 B1
(45) Date of Patent: Sep. 11, 2001

(54) METHOD AND APPARATUS FOR FRACTIONATION USING GENERALIZED DIELECTROPHORESIS AND FIELD FLOW FRACTIONATION

(75) Inventors: Frederick F. Becker, Houston; Peter R. C. Gascoyne, Bellaire; Ying Huang; Xiao-Bo Wang, both of Houston, all of TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/395,890

(22) Filed: Sep. 14, 1999

Related U.S. Application Data

(60) Continuation of application No. 09/243,348, filed on Feb. 1, 1999, now Pat. No. 5,993,632, which is a division of application No. 08/605,535, filed on Feb. 23, 1996, now Pat. No. 5,888,370.

(51) Int. Cl.$^7$ ............................. C12N 13/00; A61K 35/12

(52) U.S. Cl. .................... 435/173.9; 435/173.1; 424/520

(58) Field of Search .............................. 435/173.1, 173.9; 424/520

(56) References Cited

U.S. PATENT DOCUMENTS

| | | |
|---|---|---|
| 3,162,592 | 12/1964 | Pohl . |
| 4,001,102 | 1/1977 | Batha et al. . |
| 4,326,934 | 4/1982 | Pohl . |
| 4,440,638 | 4/1984 | Judt et al. . |
| 5,344,535 | 9/1994 | Betts et al. . |
| 5,454,472 | 10/1995 | Benecke et al. . |
| 5,489,506 | 2/1996 | Crane . |
| 5,569,367 | 10/1996 | Betts et al. . |

FOREIGN PATENT DOCUMENTS

| | | |
|---|---|---|
| 2266153A | 10/1993 | (GB) . |
| 1-196566 | 8/1989 | (JP) . |
| 5-126796 | 5/1993 | (JP) . |
| 6-18523 | 1/1994 | (JP) . |
| 474723 A | 6/1975 | (SU) . |
| WO 90 08759 A | 8/1990 | (WO) . |
| WO 91/11261 | 8/1991 | (WO) . |
| WO 93/20927 | 10/1993 | (WO) . |
| WO 94/16821 | 8/1994 | (WO) . |
| WO 94/22583 | 10/1994 | (WO) . |
| WO 95 13813 A | 5/1995 | (WO) . |

OTHER PUBLICATIONS

Arnold and Zimmerman, "Rotation of an isolated cell in a rotating electric field," *Naturwissenschaften*, 69:297–300, 1982.

Becker et al., "Separation of human breast cancer cells from blood by differential dielectric affinity," *Pro. Natl. Acad. Sci. USA*, 92:860–864, 1995.

Becker et al., "The removal of human leukaemia cells from blood using interdigitated microelectrodes," *J. Phys. D. Appl. Phys.*, 27:2659–2662–, 1994.

Davis et al., "Feasibility Study of Dielectrical Field–Flow Fractionation," *Separation Science and Technology*, 21(9):969–989, 1986.

Fuhr, *über die rotation dielektrischer körper in rotierenden feldern*, Ph.D. Dissertation, Humbolt–Universität, Berlin, Ch. 3, pp. 24–53, 1985.

Gascoyne et al., "Cell separation by conventional dielectrophoresis combined with field–flow–fractionation," 40th Annual Meeting, Baltimore, MD, p. A333, Abstract, 1996.

Gascoyne et al., "Dielectrophoretic separation of cancer cells from blood," Institute for Electrical Engineers Industrial Application Society meeting, Orlando, Florida, 1995.

Gascoyne et al., "Dielectrophoretic separation of mammalian cells studied by computerized image analysis," *Meas. Sci. Technol.*, 3:439–445, 1992.

Gascoyne et al., "Manipulation of erythroleukemia cells using travelling electric fields," *Proc. 16th IEEE–Eng. Med. Biol. Soc.*, 772–773, 1994.

(List continued on next page.)

Primary Examiner—Jon P. Weber
(74) Attorney, Agent, or Firm—Fulbright & Jaworski LLP

(57) ABSTRACT

The present disclosure is directed to a novel apparatus and novel methods for the separation, characterization, and manipulation of matter. In particular, the invention combines the use of frequency-dependent dielectric and conductive properties of particulate matter and solubilized matter with the properties of the suspending and transporting medium to discriminate and separate such matter. The apparatus includes a chamber having at least one electrode element and at least one inlet and one output port into which cells are introduced and removed from the chamber. Matter carried through the chamber in a fluid stream is then displaced within the fluid by a dielectrophoretic (DEP) force caused by the energized electrode. Following displacement within the fluid, matter travels through the chamber at velocities according to the velocity profile of the chamber. After the matter has transmitted through the chamber, it exits at the opposite end of the chamber at a characteristic position. Methods according to the invention involve using the apparatus for discriminating and separating matter for research, diagnosis of a condition, and therapeutic purposes. Examples of such methods may include separation of mixtures of cells, such as cancer cells from normal cells, separation of parasitized erythrocytes from normal erythrocytes, separation of nucleic acids, and others.

9 Claims, 9 Drawing Sheets

OTHER PUBLICATIONS

Gascoyne et al., "Numerical analysis of the influence of experimetnal conditions on the accuracy of dielectric parameters derived from electrorotation measurements," *Bioelectrochem. Bioenergetics*, 36:115–125, 1995.

Giddings, "Field–flow fractionation: analysis of macromolecular, colloidal, and particulate materials," *Science*, 260:1456–1465, 1993.

Hagedorn et al., "Travelling–wave dielectrophoresis of microparticles," *Electrophoresis*, 13:49–54, 1992.

Holzel and Lamprecht, "Dielectric properties of yeast cells as determined by elecrorotation," *Biochim. Biophys. Acta*, 1104:195–200, 1992.

Huang et al., "Application of AC electrokinetics for cell characterization and manipulation," 40th Annual Meeting, Baltimore, MD, A334, Abstract, 1996.

Huang et al., "Differences in the AC electrodynamics of viable and non–viable yeast cells determined through combined dielecrophoresis and electrorotation studies," *Phys. Med. Biol.*, 37:1499–1517, 1992.

Huang et al., "Electrokinetic behaviour of colloidal particles in travelling electric fields: studies using yeast cells," *J. Phys. D. Appl. Phys.*, 26:1528–1535, 1993.

Huang et al., "Electrorotational studies of the cytoplasmic dielectric properites of Friend murine erythroleukaemia cells," *Phys. Med. Biol.*, 40:1789–1806, 1995.

International Search Report dated Jun. 09, 1997 (UTFC:527P).

International Search Report dated Jul. 9, 1997 (UTFC:524P).

Jinsart et al., "Inhibition of Myosin Light Chain Kinase, cAMP–Dependent Protein Kinase, Protein Kinase C and of Plant CA–Dependent Protein Kinase by Anthraquinones," Biological Chemistry, 373:903–910, 1992.

Markx and Pethig, "Dielectrophoretic separation of cells: continuous separation," *Biotech. Bioeng.*, 45:337–343, 1995.

Markx et al., "Dielectrophoretic characterization and separation of micro–organisms," *Microbiol.*, 140:585–591, 1994.

Massey, In: *Mechanics of Fluids*, 2nd Edition 136–139, 1975.

Vennard, In: *Elementary Fluid Mechanics*, 150–155, 1954.

Wang et al., "A unified theory of dielectrophoresis and travelling wave dielectrophoresis," *J. Phys. D. Appl. Phys.*, 27:1571–1574, 1994.

Wang et al., "Changes in friend murine erythroleukaemia cell membranes during induced differentiation determined by electrorotation," *Biochimica et Biophysica Acta*, 1193:330–334, 1994.

Wang et al., "Dielectrophoretic manipulation of cells using spiral electrode arrays," 40th Annual Meeting, Baltimore, MD, p. A333, Abstract, 1996.

Wang et al., "Dielectrophoretic manipulation of particles," The Institute for Electrical Engineers Industrial Application Society meeting, Orlando, Florida, 1995.

Wang et al., "Non–uniform spatial distributions of both the magnitude and phase of AC electric fields determine dielectrophoretic forces," *Biochimica et. Biophysica Acta*, 1243:185–194, 1995.

Washizu et al., "Molecular Dielectrophoresis of Biopolymers," *IEEE Trans on Industry App*, 30(4):835–843, 1994.

Yeh et al., "Effects of Anthraquinones of *Polygonum cuspidatum* on HL–60 Cells, " Planta Medica, 54:413–414, 1988.

Zhang et al., "Sensitization of HER–2/Neu Overexpressing Non–Small Cell Lung Cancer Cells to Chemotherapeutic Drugs By Tyrosine Kinase Inhibitor Emodin," Oncogene, 12:571–576, 1996.

Zhang et al., "Suppressed Transformation and Induced Differentiation of HER–2/Neu Overexpressing Breast Cancer Cells By Emodin," Cancer Res., 55:3890–3896, 1995.

METHOD AND APPARATUS FOR FRACTIONATION USING GENERALIZED DIELECTROPHORESIS AND FIELD FLOW FRACTIONATION

This application is a continuation of application Ser. No. 09/243,348 filed Feb. 1, 1999, now U.S. Pat. No. 5,993,632, which is a divisional application of Ser. No. 08/605,535, filed Feb. 23, 1996, now U.S. Pat. No. 5,888,370.

BACKGROUND OF THE INVENTION

1. Field of the Invention

The present invention relates generally to the fields of molecular separation and particle discrimination. More particularly, it concerns the fractionation of particulate matter utilizing a combination of electrical, hydrodynamic or gravitational forces.

2. Description of the Related Art

The ability to identify, characterize and purify cell subpopulations is fundamental to numerous biological and medical applications, often forming the starting point for research protocols and the basis for current and emerging clinical protocols. Cell separation has numerous applications in medicine, biotechnology, and research in environmental settings. For example, cell separation can make possible life-saving procedures such as autologous bone marrow transplantation for the remediation of advanced cancers where the removal of cancer-causing metastatic cells from a patient's marrow is necessitated (Fischer, 1993). In other applications, such as the study of signaling between blood cells (Stout, 1993), (Cantrell el al., 1992), highly purified cell subpopulations permit studies that would otherwise be impossible. Current approaches to cell sorting most frequently exploit differences in cell density (Boyum, 1974), specific immunologic targets (Smeland et a., 1992), or receptor-ligand interactions (Chess and Schlossman, 1976) to isolate particular cells.

These techniques are often inadequate and sorting devices capable of identifying and selectively manipulating cells through novel physical properties are therefore desirable. The application of the principles of AC electrokinetics has been used for the dielectric characterization of mammalian cells through the method of electrorotation (ROT) (Arnold and Zimmermann, 1982; Fuhr, 1985; Holzel and Lamprecht, 1992; Wang et al., 1994) and for cell discrimination and sorting (Hagedorn et al., 1992; Huang et al., 1993; Gascoyne et al., 1992; Gascoyne et al., 1994; Huang et al., 1992). In these techniques, cells become electrically polarized when they are subjected to an AC electric field. If that field is inhomogeneous, then the cells experience a lateral dielectrophoretic (DEP) force, the frequency response of which is a function of their intrinsic electrical properties (Gascoyne et al., 1992). In turn, these properties depend strongly on cell composition and orgamization, features that reflect cell morphology and phenotype. Cells differing in their electrical polarizabilities can thus experience differential forces in the inhomogeneous electric field (Becker et al., 1994; Becker et al., 1995). Analysis of the dielectrophoretic motion of mammalian cells as a function of applied frequency permits cell membrane biophysical parameters, such as capacitance and surface conductance, to be probed. Because DEP effectively maps biophysical properties into a translational force whose direction and magnitude reflects cellular properties, some degree of separation occurs between particles of different characteristics. While DEP has been used on a microscopic scale to separate bacteria from erythrocytes (Markx et al., 1994), viable from nonviable yeast cells (Wang et al., 1993), and erythroleukemia cells from erythrocytes (Huang et al., 1992), the differences in the electrical polarizabilities of the cell types in those various mixtures were greater than those to be expected in many typical cell sorting applications.

Field flow fractionation (FFF) has also been generally employed for separation of matter, utilizing particle density, size, volume, diffusivity, thickness, and surface charge as parameters (Giddings, 1993). The technique can be used to separate many different types of matter, from a size of about 1 nm to more than about 100 micrometers which may include, for example, biological and non-biological matter. Separation according to field flow fractionation occurs by differential retention in a stream of liquid flowing through a thin channel. The FFF technique combines elements of chromatography, electrophoresis, and ultracentrifugation, and generally FFF requires the presence of a field or gradient to develop a differential flow. This differential flow creates a flow profile which may be, for example, linear or parabolic. A field is then applied at right angles to the flow and serves to drive the matter into different displacements within the flow profile which travel at differing velocities. Fields may be based on sedimentation, crossflow, temperature gradient, centrifugal forces, and the like. The technique suffers, however, from producing insufficiently pure cell populations, being too slow, or being too limited in the spectrum of target cells or other matter.

Thus, there exists a need in the art for highly discriminate separation of particulate matter, especially biological matter, that operates without physically modifying the structure of the matter to be separated. Moreover, such an approach should allow for the sensitive manipulation of such particles, which may include characterization and purification of desired matter from extraneous or undesired matter.

SUMMARY OF THE INVENTION

The present invention seeks to overcome drawbacks inherent in the prior art by combining the use of frequency-dependent dielectric and conductive properties of particles with the properties of the suspending and transporting medium. As used herein, the term "matter" is intended to include particulate matter, solubilized matter or any combination thereof. The invention provides a novel apparatus and novel methods by which different particulate matter and solubilized matter may be identified and selectively manipulated. These particles may also be collected by changing the DEP force or the fluid flow characteristics. Utilizing the invention in this manner, particulate matter and solubilized matter may be discriminated and separated. The apparatus and methods of the present invention may discriminate different types of matter simultaneously.

The present invention provides a method and apparatus for the discrimination of particulate matter and solubilized matter of different types. This discrimination may include, for example, separation, characterization, differentiation and manipulation of the particulate matter. According to the present invention, the particulate matter may be placed in liquid suspension before input into the apparatus. The discrimination occurs in the apparatus, which may be a thin, enclosed chamber. Particles may be distinguished, for example, by differences in their density, size, dielectric permittivity, electrical conductivity, surface charge, and/or surface configuration.

The methods according to the present invention may be used to discriminate particulate matter, including inorganic matter, such as minerals, crystals, colloidal, conductive, semiconductive or insulating particles and gas bubbles. The methods of the present invention may also be used to discriminate biological matter, such as cells, cell aggregates, cell organelles, nucleic acids, bacterium, protozoans, or viruses. Further, the particulate matter may be, for example, a mixture of cell types, such as fetal nucleated red blood cells in a mixture of maternal blood, cancer cells such as breast cancer cells in a mixture with normal cells, or red blood cells infested with malarial parasites. Additionally, the methods of the present invention may be used to discriminate solubilized matter such as a molecule, or molecular aggregate, for example, proteins, or nucleic acids.

Particle size to be discriminated may be any size. However, the present invention is generally practical for particles between ~10 nm and ~1 mm, and may include, for example, chemical or biological molecules (including proteins, DNA and RNA), assemblages of molecules, viruses, plasmids, bacteria, cells or cell aggregates, protozoans, embryos or other small organisms, as well as non-biological molecules, assemblages thereof, minerals, crystals, colloidal, conductive, semiconductive or insulating particles and gas bubbles. For biological applications using living cells, the present invention allows cells to be separated without the need to alter them with ligands, stains, antibodies or other means. Cells remain undamaged, unaltered and viable during and following separation. Non-biological applications similarly require no such alteration. It is recognized however, that the apparatus and methods according to the present invention are equally suitable for separating such biological matter even if they have been so altered.

The apparatus may include, for example, a chamber. The chamber may have at least one inlet and one outlet port, an interior surface and an exterior surface. The chamber may further be designed to have structural characteristics which cause a fluid or gas travelling through the chamber to travel at differing velocities according to a velocity profile. The chamber may be rectangular in shape and may include, for example, a top wall, bottom wall and two side walls. In certain embodiments, the chamber may be constructed so that the top wall and bottom wall are of a much greater magnitude than the side walls, thereby creating a thin chamber capable of creating a velocity profile. In other embodiments, the chamber may be constructed so that the top wall and bottom wall are of a much smaller magnitude than the side walls, again creating a thin chamber capable of creating a velocity profile. Alternately, the chamber may be of circular construction, triangular, rectangular, hexadecagonal, or of other geometrical shapes. As such, the present invention is not intended to be limited to a particular geometric shape. The chamber according to the present invention may be constructed of many different materials, for example, glass, polymeric material, plastics, quartz, coated metal, or the like.

The chamber includes at least one electrode element adapted along a portion or all of the chamber. Each of these one or more electrode elements may be electrically connected to an electrical conductor. In the discussion which follows, the terms "electrode element" or "electrodes" will be used. As used herein, "electrode element" is a structure of a highly electrically-conductive material over which an applied electrical signal voltage is constant. The electrode elements may be any appropriate geometric shape such as, for example, castellated, rectangular, and the like. It is to be understood that these terms include all of the below described electrode configurations. An electrical signal generator, which may be capable of varying voltage, frequency, phase or any combination thereof, may transmit at least one electrical signal to the electrode elements. The electrode elements of the present invention may include, for example, a plurality of electrode elements which may be connected to a plurality of electrical conductors, which in turn is connected to the electric signal generator.

The chamber according to the present invention may include a plurality of electrode elements which comprise an electrode array. As used herein, an "electrode array" is a collection of more than one electrode element in which each individual element may be displaced in a well-defined geometrical relationship with respect to one another. This array may be, for example, a parallel array, interdigitated castellated array, a polynomial array, plane electrode, or the like. Further, the array may be comprised of microelectrodes of a given size and shape, such as an interdigitated array. The electrode array may be adapted along any interior or exterior surface of the chamber. Alternately, it is envisioned that the electrode array may be incorporated into the material which comprises the chamber walls. In certain embodiments, the electrode array may be a multilayer array in which conducting layers may be interspersed between insulating layers. Fabrication of such an electrode array is known in the art, and is similar to the fabrication of multilayer printed circuit boards. Further, the present invention may have a plurality of electrode arrays which may be adapted, for example, on opposing surfaces of the chamber. However, it may be possible to place the plurality of electrode arrays on adjacent surfaces or on all surfaces of the chamber.

The electrode elements may be adapted to be substantially longitudinally or latitudinally along a portion of the chamber. Other configurations of electrode elements are contemplated by the present invention, such as electrode elements adapted at angles to the chamber. It is also possible to use a three-dimensional electrode element that may or may not be attached to the surface of the chamber. For example, electrode elements may be fabricated from silicon wafers, as is known in the art. If the electrodes are adapted along the exterior surface of the chamber, it is envisioned that a means of transmitting energy into the chamber, such as a microwave transmitter may be present. The electrode elements may be configured to be on a plane substantially normal or parallel to a flow of fluid travelling through said chamber; however, it is to be understood that the electrode elements may be configured at many different planes and angles to achieve the benefits of the present invention.

When the electrode elements are energized by at least one electrical signal from the electrical signal generator, the electrode elements thereby create a spatially inhomogeneous alternating electric field, which may cause a DEP force on the particulate matter and solubilized matter having components normal to the fluid travelling through the chamber. This DEP force may be a conventional DEP force (cDEP), which may act in different directions with respect to the fluid, depending on the configuration of the electrode elements. The cDEP force typically acts in a direction substantially normal to the electrode element plane, that is, the cDEP force typically forces matter towards or away from this plane. In certain embodiments, the DEP force may act solely in a direction normal to the fluid. As used herein, "a direction normal to the fluid" means in a direction which is substantially non-opposing and substantially non-linear to the flow of a fluid traveling through the chamber. This direction may be for example, vertically, sideways, or in another non-opposing direction. By effect of this DEP force, the particulate matter and solubilized matter may be displaced to positions within the fluid. This displacement may be relative to the electrode elements, or may relate to other references, such as the chamber walls.

The ratio of electrode element width to electrode element spacing may be modified to change the particulate matter and solubilized matter levitation height. That is, as used herein, "levitate" or "levitation height" means that matter is displaced at different levels with respect to the electrode elements, in any direction. Specifically, by changing this ratio, the electric field which is created is thereby altered. When the electric field is thereby altered, in magnitude and/or inhomogeneity, the levitation height of the matter similarly changes. This levitation need not be in a vertical direction, and may include displacement in a horizontal direction, for example.

In the present invention, the cDEP force is dependent on the magnitude of the spatial inhomogeneity of the electric field and the in-phase (real) part of the electrical polarization induced in matter by the field. It is to be understood that the term "electrical polarization" is related to the well-known Clausius-Mossotti factor, described below. This field-induced electrical polarization is dependent on the differences between the dielectric properties between the matter and the suspending medium. These dielectric properties in general are represented by dielectric permittivity and electrical conductivity. The combination of these two properties is known as complex permittivity. The DEP force causes the matter to move towards or away from regions of high electrical field strength, which in an exemplary embodiment, may be towards or away from the electrode plane.

The equation for the time-averaged conventional dielectrophoretic force in an electric field strength having an rms value of $E_{rms}$ is:

$$F(t)=2\pi\epsilon_m r^3 Re[f_{cm}]\nabla E_{rms}^2 \quad (1)$$

where the factor $f_{cm}$ is the well-known Clausius-Mossotti factor defined as $f_{cm}(\epsilon_p^*,\epsilon_m^*)=(\epsilon_p^*-\epsilon_m^*)/(\epsilon_p^*+2\epsilon_m^*)$, and where $\epsilon_p^*$ and $\epsilon_m^*$ are the complex permittivities of the matter and its suspending medium, respectively. The Clausius-Mossotti factor may also include other terms to account for other forms of electrical polarization or conductivity induced or modified by the applied field, for example, the surface charge of the matter. In the force equation, r is the radius of the matter desired to be discriminated, $Re[f_{cm}]$ is the real part (in-phase component) of the factor $f_{cm}$, and $\nabla E_{rms}^2$ is the magnitude non-uniformity factor of the applied electric field. As seen from equation (1), if the in-phase part of the Clausius-Mossotti factor is greater than zero, then the matter tends to move towards the strong field. If the in-phase part of the Clausius-Mossotti factor is less than zero, the matter tends to move towards the weak field.

In an alternate embodiment of the present invention, the electrode array may include at least three sets of electrode elements. As used herein, "set" is a group of individual electrode elements having a defined geometric relationship to each other. Such a defined geometrical relationship may include, for example, a triangle, circle, square, or complex shapes such as conic sections, and the like. It is to be understood that sets of electrode elements may be designed based on principles of electromagnetic theory. At least one applied electrical signal having different phases may be applied to the at least three sets of electrode elements. For example, one applied signal may be adequately delayed by a capacitor or other time delay circuitry to provide each of the at least three sets of electrode elements a signal having a different phase. Alternatively, different signals having different phase relationships may be provided to the electrode elements. These signals thus create an electric field distribution that may be spatially inhomogeneous with respect to magnitude, and may travel through space by virtue of the phase distribution.

It is noted that by applying at least one electrical signal having different phases to the at least three sets of electrode elements, a traveling wave dielectrophoretic (twDEP) force is created in addition to the cDEP force. The twDEP force is dependent upon the phase distribution of the applied electric field (reflecting its movement through space, which is in the direction of small phase regions), and the out-of-phase (imaginary) part of the electrical polarization induced in the matter by the field. The twDEP force causes the matter to move towards or away from the direction of increasing phase values. The twDEP force typically acts in a direction substantially parallel to the electrode element plane. In the case of twDEP, the equation for the time-averaged travelling wave dielectrophoretic force is:

$$F(t)=2\pi\epsilon_m r^3 Im(f_{cm})(E_{x0}^2\nabla\Phi_x+E_{y0}^2\nabla\Phi_y+E_{z0}^2\nabla\Phi_z) \quad (2)$$

where $Im(f_{cm})$ is the imaginary part (out-of-phase component) of the factor $f_{cm}$, and $E^2\nabla\Phi$ is the phase non-uniformity factor (where $E_{x0}$, $E_{y0}$ and $E_{z0}$ are the magnitudes of each electric field component in the Cartesian co-ordinate frame, and $\Phi_x$, $\Phi_y$, and $\Phi_z$, are the phases of each field component). As seen from Equation (2), if the out-of-phase part of the Clausius-Mossotti factor is greater than zero, the force directs matter towards regions where the phases of the field components are larger. If the out-of-phase part of the Clausius-Mossotti factor is less than zero, the force directs matter towards regions where the phases of the field components are smaller.

The combination of the cDEP and twDEP forces is referred herein as generalized dielectrophoresis (gDEP). The combination of equations (1) and (2) therefore results in the equation for the time-averaged generalized dielectrophoretic force:

$$F(t)=2\pi\epsilon_m r^3 (Re[f_{cm}]\nabla E_{rms}^2+Im(f_{cm})(E_{x0}^2\nabla\Phi_x+E_{y0}^2\nabla\Phi_y+E_{z0}^2\nabla\Phi_z)) \quad (3)$$

Thus, matter under the influence of one or both of these forces may be displaced to different positions within the fluid flowing in the chamber. It is noted that the cDEP force may be approximately four times greater than the twDEP force caused by the same electrical field strength. It is to be understood that cDEP and twDEP are principal components of gDEP, and other gDEP forces such as a combination of CDEP and twDEP, may also act on matter in an apparatus according to the present invention.

In an embodiment of the present invention which utilizes twDEP forces in addition to cDEP forces, matter may be displaced in two-dimensions (time and horizontal). As discussed above, the cDEP force combined with field flow fractionation causes the matter to be displaced to different positions within the fluid flow. In addition, in an embodiment in which the electrode elements are configured substantially parallel to the fluid flow through the chamber, the twDEP force on matter acts substantially parallel to the plane of the electrode elements, and substantially transverse to the fluid flow. Therefore, matter is deflected laterally across the chamber from the original narrow flow stream in which it entered the chamber. The direction and magnitude of this deflection is a measure of the imaginary part of the dielectric properties of the matter, namely the electrical polarization induced in the matter by the field. The deflected matter therefore travels through the chamber and exits at positions that are laterally displaced from the port through which it entered.

Thus, the combined influence of the cDEP and twDEP forces results in a time and horizontal displacement of matter. Each component of the displacement represents different characteristics of the introduced matter, and matter having different characteristics may experience different components of force in each direction. Therefore, matter discrimination may be achieved according to the time of travel through the chamber depending on the in-phase (real) part of the polarization of the matter, its density, surface configuration, volume, and the dielectric properties of the fluid. Matter discrimination according to the lateral displacement of the matter from its inlet position depends on its volume and the out-of-phase (imaginary) part of its electrical polarization, and the dielectric properties of the fluid. The outlet port may be constructed so that matter having different lateral positions at one displacement level may be separately discriminated. For example, it may be possible to utilize a laser as a tool to determine characteristics of matter exiting at selected lateral positions.

Common electrical conductors may be used to connect the one or more sets of electrode elements to the signal generator. The common electrical conductors may be fabricated by the same process as the electrodes, or may be one or more conducting assemblies, such as a ribbon conductor, metallized ribbon or metallized plastic. A microwave assembly may also be used to transmit signals to the electrode elements from the signal generator. All of the electrode elements may be connected so as to receive the same signal from the generator. It is envisioned that such a configuration may require presence of a ground plane. More typically, alternating electrodes along an array may be connected so as to receive different signals from the generator. The electrical generator may be capable of generating signals of varying voltage, frequency and phase and may be, for example, a function generator, such as a Hewlett Packard generator Model No. 8116A. Signals desired for the methods of the present invention are in the range of about 0 to about 15 volts, and about 0.1 kHz to about 180 MHz, and more preferably between about 0 to about 5 volts, and about 10 kHz to 10 MHz. These frequencies are exemplary only, as the frequency required for matter discrimination is dependent upon the conductivity of, for example, the cell suspension medium. Further, the desired frequency is dependent upon the characteristics of the matter to be discriminated. The discrimination obtained depends on the shape, size and configuration of the electrode elements, for example. In an exemplary embodiment, the signals are sinusoidal, however it is possible to use signals of any periodic or aperiodic waveform. The electrical signals may be developed in one or more electrical signal generators which may be capable of varying voltage, frequency and phase.

A chamber according to the present invention may have at least one inlet and outlet port. These ports may be the same port, or the chamber may be constructed to have different ports. The outlet port may be arranged to be vertically lower than the at least one inlet port. Such an arrangement thereby permits sedimentation of the particulate matter and solubilized matter as it travels throughout the chamber. In addition to the at least one inlet port and one outlet port, the chamber may also include one or more input ducts which allow the fluid to flow through the apparatus.

The outlet port of the chamber according to the present invention may take many forms. Specifically, the outlet port may be a single port, or a plurality of ports, or an array of ports. The outlet port, for example, may be located along the entire width or a part of the width of the chamber. The outlet port may be adapted to receive matter of various shapes and sizes. For example, the size of the outlet port may vary from approximately twice the size of the matter desired to be discriminated to the entire width of the chamber. In one embodiment, the outlet port may be constructed of one or more tubing elements, such as TEFLON tubing. The tubing elements may be combined to provide an outlet port having a cross section comprised of individual tubing elements. Further, for example, the outlet port may be connected to fraction collectors or collection wells which are used to collect separated matter. As used herein, "fraction collectors" and "collection wells" include storage and collection devices for discretely retaining the discriminated particulate and solubilized matter. Other components that may be included in the apparatus of the present invention are, for example, measurement or diagnostic equipment, such as cytometers, lasers, particle counters and spectrometers.

After being displaced within the fluid travelling through the chamber of the present invention, the displaced matter may exit from the outlet port or ports at a time proportionate to the displacement of the matter within the fluid. Specifically, matter at different levels of displacement within the fluid travels at different speeds. Therefore, the displaced matter is discriminated by its displacement within the fluid flow. The position of the particulate matter and solubilized matter within the fluid causes the matter to travel through the chamber at velocities according to the velocity profile of the chamber.

This velocity profile may be, for example, a hydrodynamic fluid profile such as a parabolic flow profile. The velocity profile may be determined by knowing the flow rate of the fluid, and the chamber width and thickness. The velocity profile may then be calculated according to the equation:

velocity profile=(flow rate)/(chamber width×chamber thickness).(4)

Parameters that determine the velocity profile of the fluid flow include (but are not limited to): the chamber width or thickness, which in a rectangular embodiment may be the distance between opposing walls; constrictions or expansions of the fluid flow path which may include, for example, those arising for a nonparallel disposition of opposing chamber walls, or from the presence of suitably-placed obstructions or vanes; surface roughness of the chamber walls; structural features of the chamber walls that give rise to periodic or aperiodic modifications of the thickness of the fluid stream, including the electrode elements and other surface structural configurations, and the geometrical form of the chamber which may be, for example, rectangular, circular, wedge-shaped, stepped, or the like.

Embodiments of the present invention may have, for example, one inlet port adapted to receive the particulate matter to be discriminated. The inlet port may be located, for example, close to the top of one end of the chamber. This apparatus may also include one or more ducts to introduce a fluid that travels through the chamber. The ducts, which may be arranged substantially along the entire width of the input end of the chamber, serve to introduce a sheet of fluid that travels throughout the chamber in a substantially linear direction. As used herein, a "sheet" of fluid may be a flow of fluid or gas entering the chamber at a substantially uniform flow rate. The introduced fluid carries the particulate matter through the chamber. Following transit through the chamber, fluid leaves at the opposite end. This exit end of the chamber may include, for example, one or more exit ports, which may be arranged in one or more arrays of exit ports.

Different electrical signals (frequency or magnitude or both) may be applied to electrode elements located on each of the side walls. There is a synergistic interaction between these different electrical signals which creates an inhomogeneous electric field. Different matter equilibrates at different characteristic distances from the side walls of the chamber based on this synergistic interaction of the differing electrical signals, herein an "equilibrium position." The equilibrium position is therefore caused by cDEP forces on the particles. Additionally, twDEP forces may impact this equilibrium position. This equilibration position depends on the dielectric and conductive properties of the matter, the magnitude and frequency of the electrical fields applied to the electrodes on the opposing chamber walls, fluid density, viscosity, and flow rate. The equilibrium position of matter depends on the synergism of the different electrical signals acting within the chamber to levitate the matter. The velocity of the different matter within the fluid is controlled by the velocity profile of the fluid. This velocity profile has a maximum rate towards the center of the chamber, with this rate proportionately diminishing as distance from the side walls decreases. Because of this velocity profile, matter that has equilibrated at different equilibrium distances from the chamber walls will be carried at different velocities and therefore take varying amounts of time to traverse the chamber.

The distance that matter sediments during its passage across the chamber will depend upon its transit time, as gravitational forces act on the matter during its transit through the chamber, and is known as a "sedimentation effect." Consequently, different particles will sediment to different depths based upon the transit time of matter through the chamber. Particle sedimentation also depends on matter characteristics, such as size, mass, and volume, for example. Therefore, the time required for particles to travel across the entire length of the chamber is controlled by the fluid flow profile. The placement of particles within the fluid flow profile is in turn determined by the synergism of the differing electrical signals. Particles with different characteristics may exit the chamber through different outlet ports which may be placed at different heights with respect to the inlet ports. Discrimination may be accomplished either in "batch mode" or in continuous modem. In batch mode, an aliquot of particles is injected and collected with respect to the time of transit for the particles and the height of exit at the outlet ports. In continuous mode, a constant stream of particles is injected into the inlet port, and matter emerging at different heights are continuously collected.

A further embodiment of the chamber having two facing electrode arrays adapted on opposing surfaces is also possible. In this design, the electrode arrays are arranged along the opposing surfaces so that the individual electrode elements are substantially parallel to the direction of fluid flow. However, it may be possible to create the desired DEP forces by electrodes perpendicular or in other directions to the flow of fluid. Different electrical signals (frequency, magnitude, and phase, or a combination thereof) may be applied to the facing electrodes from the signal generator so that particles experience different cDEP and/or twDEP forces. The cDEP forces may act to displace matter to or away from the electrode plane, based on the magnitude of the field inhomogeneity. The twDEP forces may act in a plane substantially parallel to the electrode arrays, based on the phase inhomogeneity of the field produced by the electrode arrays.

The cDEP forces in combination with field flow fractionation cause matter to be displaced characteristic distances with respect to the electrode arrays. This characteristic distance is a function of the matter's dielectric and conductive properties, the magnitude and frequency of the electrical fields applied to the electrodes on the facing chamber walls, and the fluid density, viscosity and flow rate. Matter therefore equilibrates at an equilibrium position with respect to the electrode arrays dependent on these characteristics. Because of the velocity profile set up in the chamber, matter at different equilibrium positions travels at different velocities and therefore takes different amounts of time to travel through the chamber.

In a further embodiment, the electrode arrays may be arranged on opposing vertical walls of the chamber. In this embodiment, the electrode arrays may be arranged at right angles to the flow of fluid through the chamber. In addition to displacement caused by the DEP forces, matter also sediments as it travels through the chamber and the distance that the matter sediments depends upon the time required to traverse the chamber and the sedimentation rate of the matter. The distance of matter sedimentation is also affected by the twDEP force. Specifically, the twDEP force acts in a substantially vertical direction when the electrode arrays are located on the side walls of the chamber. Therefore the twDEP force component adds to or opposes the sedimentation forces acting on the matter. Thus the net vertical displacement which the matter experiences as it traverses the chamber is modified.

Matter discrimination in this embodiment may be accomplished in a continuous mode, whereby a constant stream of matter is injected into the at least one inlet port, and matter emerging at differing vertical displacements is continuously collected at the outlet ports. Alternately, it may be possible to operate this embodiment in a "pulse" mode. In pulse mode, a batch of matter may be injected into the at least one inlet chamber and electrical signals are applied for a defined amount of time. Then the signals are turned off, and the matter is allowed pass through the chamber under the influence of the fluid flow and be collected at the at least one outlet port. Then, another batch may be injected for similar processing.

To further achieve the benefits of discrimination, the carrier fluid characteristics at different vertical displacements may be varied by modifying for example, flow rate, fluid density, viscosity, dielectric permittivity, pH and conductivity of the carrier fluid. In this way, additional matter characteristics may be exploited for particular discrimination applications.

The methods and apparatus of the present invention introduce for the first time the use of the frequency-dependent dielectric and conductive properties of particles as well as those of the suspending medium. These new criteria for particle fractionation allow sensitive manipulation of particles because the dielectrophoretic force is large and strongly dependent on particle properties. Appropriate choices of the suspending medium and applied field conditions allow for high levels of discrimination.

Previously reported field flow fractionation techniques have limitations for biological samples because of the narrow range of particle densities, demanding complex centrifuges and centrifugation techniques for good discrimination. The cDEP affinity method demands large differences in the dielectric characteristics of the particles to be separated so that selected particulate matter and solubilized matter can be completely immobilized while others are swept away by fluid flow forces. Since, for biological cells, damage can occur at high electric field strengths, there is a practical limitation to the maximum cDEP force that can be applied and this in turn limits the maximum fluid flow rate in the cDEP affinity approach. This may result in a slow cell sorting rate. In the methods of the present invention, these limitations are substantially reduced. Furthermore, the cDEP affinity method of the prior art utilizes the dielectrophoretic force component that generally immobilizes particles on electrode elements. The cDEP/FFF approach of the present invention utilizes the cDEP component in a direction which may be normal to the flow.

Also, in the present invention, the flow profile is an active mechanism for the separation and discrimination of particles, and the dielectrophoretic force (mainly the force component in the direction normal to the fluid flow profile) is the primary means by which the height of particles in the fluid stream is controlled. As discussed above, the fluid profile may be controlled by apparatus design, fluid velocity, density and the like. By combining FFF and dielectrophoretic forces, the present invention takes advantage of particle volume and density in synergism with the frequency-dependent particle dielectric and conductive properties as well as surface configuration. The operation of an apparatus according to the present invention may be controlled by varying experimental conditions including, but not limited to, the particle suspending medium conductivity and permittivity, the fluid flow rate, viscosity and density, the applied electrical field strength and the applied frequency. This utilization of many parameters in setting the operational conditions for fractionation greatly increases the ability to discriminate between different particulate matter and solubilized matter. In the methods according to the present invention, particles emerging from the outlet ports of the apparatus may be collected, for example, by one or more fraction collectors. Furthermore, when necessary or desired, particles may be transferred to collection wells containing appropriate solutions or media, such as neutral salt buffers, tissue culture media, sucrose solutions, lysing buffers, solvents, fixatives and the like.

In an illustrative embodiment, the chamber may be constructed in a rectangular shape using, for example, two glass slides as chamber walls. These chamber walls may be spaced apart by spacers to create the rectangular design. These spacers may be made of, for example, glass, polymeric material such as TEFLON, or any other suitable material. The size of the chamber and spacing between chamber walls is dependent on the size of the particles which are to be discriminated. To practice the methods of the present invention, an apparatus may have spacing between about 100 nm and about 1 mm, and more preferably between about 20 microns and about 200 microns in an illustrative embodiment for the purpose of discriminating mammalian cells. Further, a longer chamber may be desired to permit greater discrimination throughput. An apparatus according to the present invention can discriminate cells at a rate between about 1000 and about 3 million cells per second. Factors that determine discrimination rate include, for example, the dielectric properties of the particles to be discriminated, the electrode design, length of the chamber, fluid flow rate, and frequency and voltage of the electrical signals. The chamber dimensions may be chosen to be appropriate for the input matter type, characteristics, and degree of discrimination desired or required.

In other embodiments, one or more surfaces of the chamber may support an electrode array. The electrode array may be a microelectrode array of, for example, parallel electrode elements. In certain embodiments, the electrode elements may be spaced about 20 microns apart. The apparatus may accommodate electrode element widths of between about 0.1 microns and about 1000 microns, and more preferably between about 1 micron and about 100 microns for embodiments for the discrimination of cellular matter. Further, electrode element spacing may be between about 0.1 microns and about 1000 microns, and for cellular discrimination more preferably between about 1 micron and about 100 microns. Alteration of the ratio of electrode width to electrode spacing in the parallel electrode design changes the magnitude of the dielectrophoretic force and thereby changes the particle levitation characteristics of the design. The electrode elements may be connected to a common electrical conductor, which may be a single electrode bus carrying an electrical signal from the signal generator to the electrode elements. Alternately, electrical signals may be applied by more than one bus which provides the same or different electrical signals. In certain embodiments, alternate electrode elements may be connected to different electrode buses along the two opposite long edges of the electrode array. In this configuration, alternate electrode elements are capable of delivering signals of different characteristics. As used herein, "alternate electrode elements" may include every other element of an array, or another such repeating selection of elements. The electrode elements if may be fabricated using standard microlithography techniques that are well known in the art. For example, the electrode array may be fabricated by ion beam lithography, ion beam etching, laser ablation, printing, or electrodeposition. The array may be comprised of for example, a 100 nm gold layer over a seed layer of 10 nm chromium.

An apparatus according to the present invention may be used with various methods of the present invention. For example, an apparatus according to the present invention may be used in a method of discriminating palate matter and solubilized matter utilizing dielectrophoresis and field flow fractionation. This method includes the following steps. First, a carrier medium, such as a cell suspension medium, tissue culture medium, a sucrose solution, or the like, which may include the matter to be discriminated, may be introduced into one or more inlet ports of the chamber. This introduction causes the carrier medium to travel through the chamber according to a velocity profile. At least one alternating electrical signal may be applied to the one or more electrode elements at different phases, which creates a travelling electric field, which may also be spatially inhomogeneous, within the chamber. As used herein, "different phases" means 'that adjacent electrode elements within an array may receive signals having different phases. However, many electrode elements may receive signals of the same phase. For example, four adjacent electrode elements may receive signals of 0°, 90°, 180° and 270° respective phase. The next four adjacent electrode elements may receive signals having this same phase relationship. Many other such phase relationships between electrode elements may be used, and the sequence and number of electrode elements which have the same phase may be varied.

The field created by the different phases causes the matter within the chamber to be displaced to positions within the carrier medium. Thus, the matter is discriminated according to its positions within the carrier medium. Specifically, the matter may be discriminated, for example, according to the velocity profile of the carrier medium, because the velocity profile of the carrier medium causes the carrier medium at different positions within the chamber to travel at differing velocities. To further discriminate matter, the electrical signal may be varied (frequency, magnitude, phase or any combination thereof). Such a change thereby causes a change in the travelling alternating electric field which, in turn, changes the displacement of the matter.

Another method according to the present invention includes discriminating particulate matter and solubilized matter utilizing dielectrophoresis and field flow fractionation according to the following steps. First, the matter is introduced into at least one inlet port of a chamber according to the present invention. Next, a transport fluid, which may be, for example, a tissue culture medium or a gas, is introduced into at least one duct. The effect of this fluid in the chamber causes a fluid flow in the chamber at a speed according to the velocity profile within the chamber. At least one electrical signal is applied to electrode elements at different phases. These energized electrodes thereby create a travelling electric field, which may also be spatially inhomogeneous, within the chamber. The field causes a DEP force on the matter causing the matter to be displaced to a position within the transport fluid. As this transport fluid is subjected to a velocity profile, the matter is thereby partitioned according to its position within the transport fluid flow. It is further possible to collect the matter at one or more outlet ports. Moreover, the matter may be collected at a time dependent upon the velocity profile of the transport fluid.

There are further steps possible to more precisely discriminate matter. These steps include the following. First, the alternating electrical signal or signals may be selected at a frequency and voltage combination which causes the matter to be either attracted towards or repelled from the electrode elements. By doing so, the matter is more clearly displaced within the transport fluid. By application of such a voltage and frequency combination, it is possible to hold the matter in close proximity to the electrode elements.

It is possible to select a frequency to attract desired or nondesired matter. As used herein, desired matter may be any matter which is desired to be discriminated and collected for further use. For example, the separation of normal blood cells from a sample including cancer cells may be desired for use in returning these normal cells into a patient's bloodstream. Nondesired matter may be matter which is desired to be discriminated for other purposes. For example, cancer cells from a patient's blood or bone marrow may be discriminated so that a sample of blood not containing the cancer cells may be returned to the patient.

A method for discriminating such a combination of matter may include the following. A frequency is select so that the nondesired matter is held in close proximity to the electrode elements and the desired matter is partitioned from the nondesired matter by the fluid flow. This frequency may be known as a holding agency. The fluid flow then carries the desired matter to the outlet port or ports of the chamber, where it may be collected. After collection, the desired matter may, for example, be returned to a patient's bloodstream or bones, or it may be used in a diagnostic manner. Then, to clear the chamber, the frequency may be changed, or the voltage itself may be turned off. This will cause the nondesired matter to be released from close proximity to the electrode element and will be partitioned by the fluid flow. This nondesired matter may then flow through the chamber in the fluid, and may be collected, if desired. After collection, the nondesired matter may be used, for example, for diagnosis or other purposes.

In an alternate embodiment, it may be possible to hold desired matter in close proximity to the electrode elements, and first partition the nondesired matter by the fluid flow, following the same steps outlined above.

The apparatus and methods of the present invention may be used for a number of different useful manners. For example, the methods according to the present invention may be used to determine characteristics of an unknown particulate matter and unknown solubilized matter in a sample of matter. These characteristics can then be compared to known matter. Additionally, the methods of the present invention may be used to diagnose a condition by determining a presence of unidentified particulate matter and unidentified solubilized matter in a patient sample. This unidentified matter may be, for example, the presence of a cancer, a virus, parasite, or the like. After determining the presence of a condition, the methods of the present invention may be used to treat the condition by using an apparatus according to the present invention to discriminate the cancer, virus, parasite or the like from normal blood or bone marrow cells.

"Manipulation" as used in relation to the present invention may include, for example, characterization, separation, fractionation, concentration and/or isolation. Typical biological applications for the device useful for specific products and services include the manipulation of tumor cells, such as epithelial tumor cells or leukemia cells, from blood and hemopoietic stem cells, purging of tumor cells from bone marrow and hemopoietic stem cells and mixtures with other normal cells, purging of residual T-lymphocytes from stem cells, and enrichment of specific target cell types including tumor cells, stem cells, etc. Also included is the manipulation of leukocyte cell subpopulations, removal and concentration of parasitized erythrocytes from normal erythrocytes in malaria and of other parasitized cells from their normal counterparts, manipulation of cells at different phases of the cell cycle, manipulation of viable and nonviable cells, manipulation of free cell nuclei, and manipulation of nucleated fetal erythrocytes from maternal blood for further analysis including genetic testing. Moreover, the invention contemplates the manipulation of bacteria, viruses, plasmids and other primitive organisms from water, blood, urine, cell mixtures and other suspensions, manipulation and identification of tumor cells in biopsies, plaques and scrape tests including Pap smears, and the manipulation and identification of metastatic tumor cells from cell mixtures.

With different and smaller electrode geometries, it is contemplated that the technology can be used for molecular applications including manipulation of DNA or RNA molecules and/or DNA or RNA fragments according to their molecular weight, folding characteristics and dielectric properties, manipulation of chromosomes, manipulation of specific protein/DNA and protein/RNA aggregates, manipulation of individual proteins from a mixture, and manipulation of specific subcellular molecular complexes and structures.

In order to optimize particle discrimination in different applications it is understood that the present invention may encompass use of specifically-targeted electrodes and chamber designs. These designs should provide a sensitive dependency of the height of particle levitation on the particle dielectric properties. For example, alteration of the ratio of electrode width to electrode spacing in the parallel electrode design changes the vertical component of the dielectrophoretic force and thereby changes the particle levitation characteristics of the design. Other strategies for providing improved particle discrimination include, for example, using more than two sets of electrode elements with different frequencies and/or voltages applied to them and the exploitation of synergism between electrical signals applied to electrode arrays on both the chamber bottom and top walls. In addition, dielectric (i.e. non-conducting) elements can be placed within the chamber to modify both the electrical field distribution and the hydrodynamic flow profile. The electrode element size and shape may be designed to optimize discrimination. Furthermore, several electrode geometries (energized with the same or different electrical signals) can be connected serially so as to provide for stepwise discrimination between different particulate matter and solubilized matter. Different chamber configurations can also be used in series. Finally, cells that have been separated by an upstream cDEP/FFF or gDEP/FFF configuration can be collected and held downstream by cDEP or gDEP trapping for characterization.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

PIG. 1B is a block diagram of an apparatus according to the present invention in which an electrode array is positioned normal to a fluid flow.

Figure 1A:
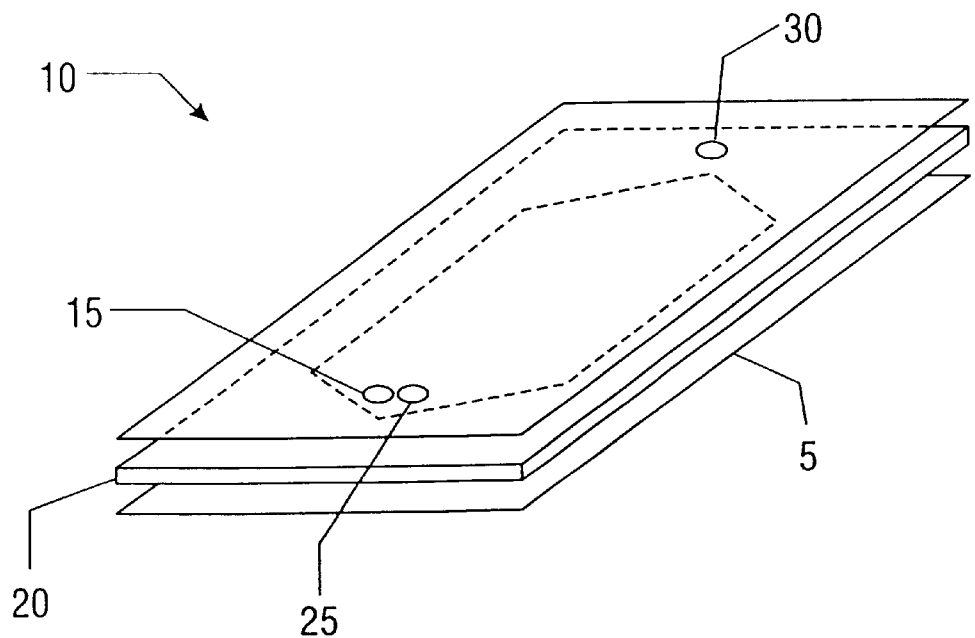
FIG. 1A is a block diagram of an apparatus according to the present invention.
Figure 1B:
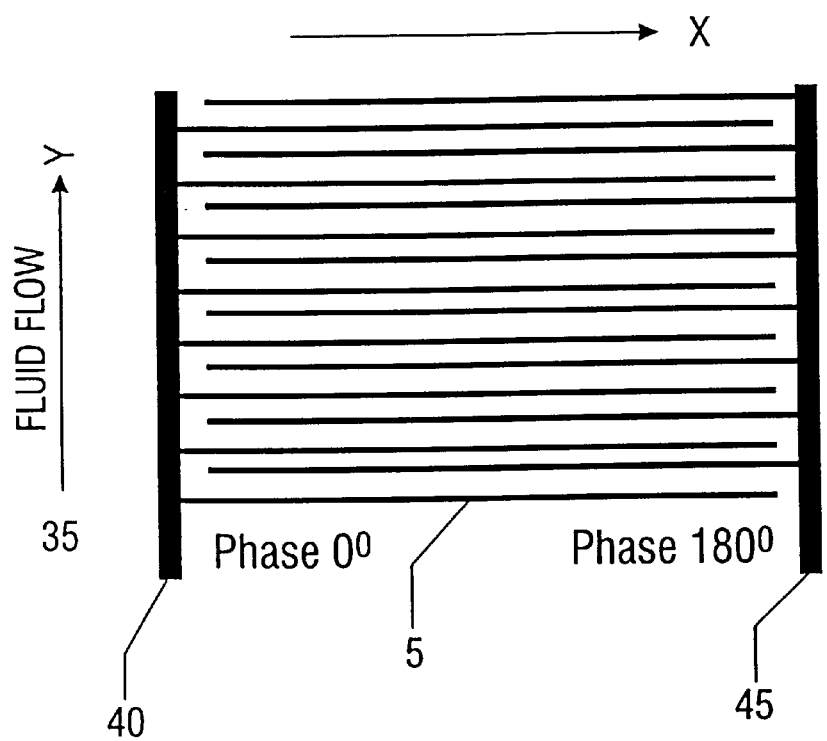
Figure 1C:
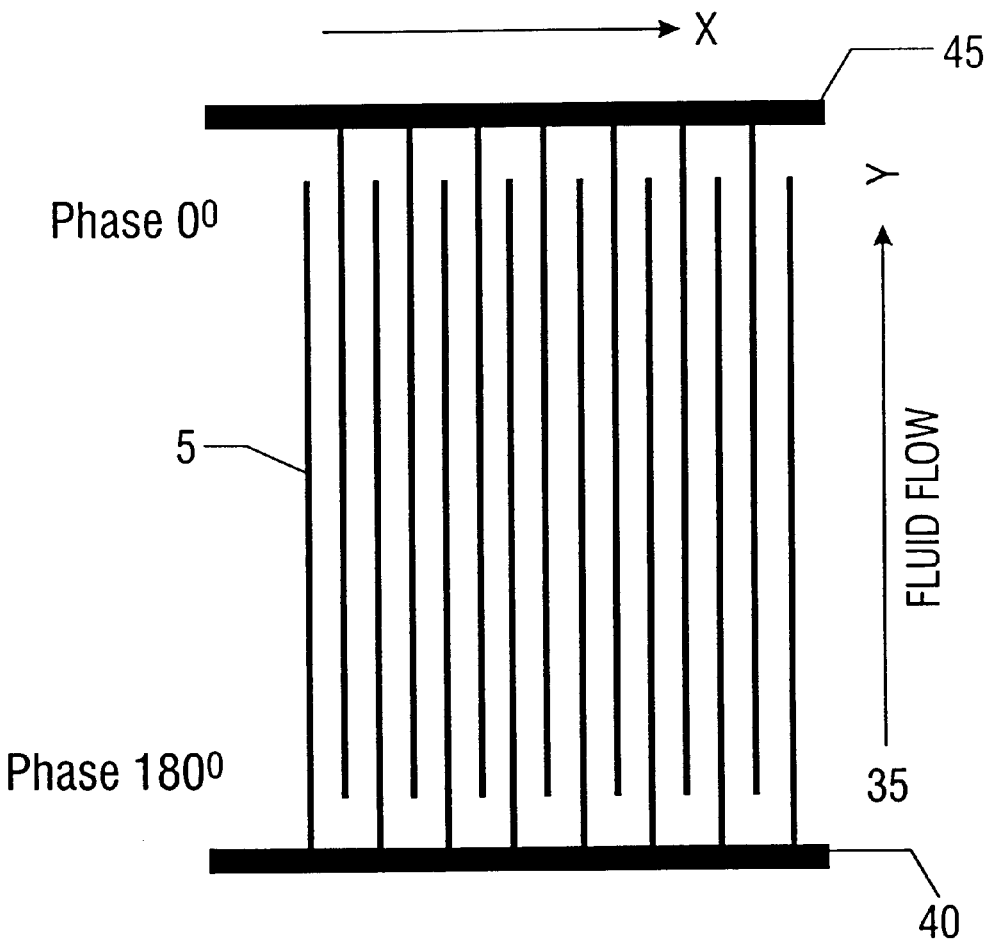

FIG. 1C is a block diagram of an apparatus according to the present invention in which an electrode array is positioned parallel to a fluid flow.

PIG. 2A is a side view of an apparatus according to the present invention which describes a typical trajectory of matter introduced into the apparatus.

Figure 2A:
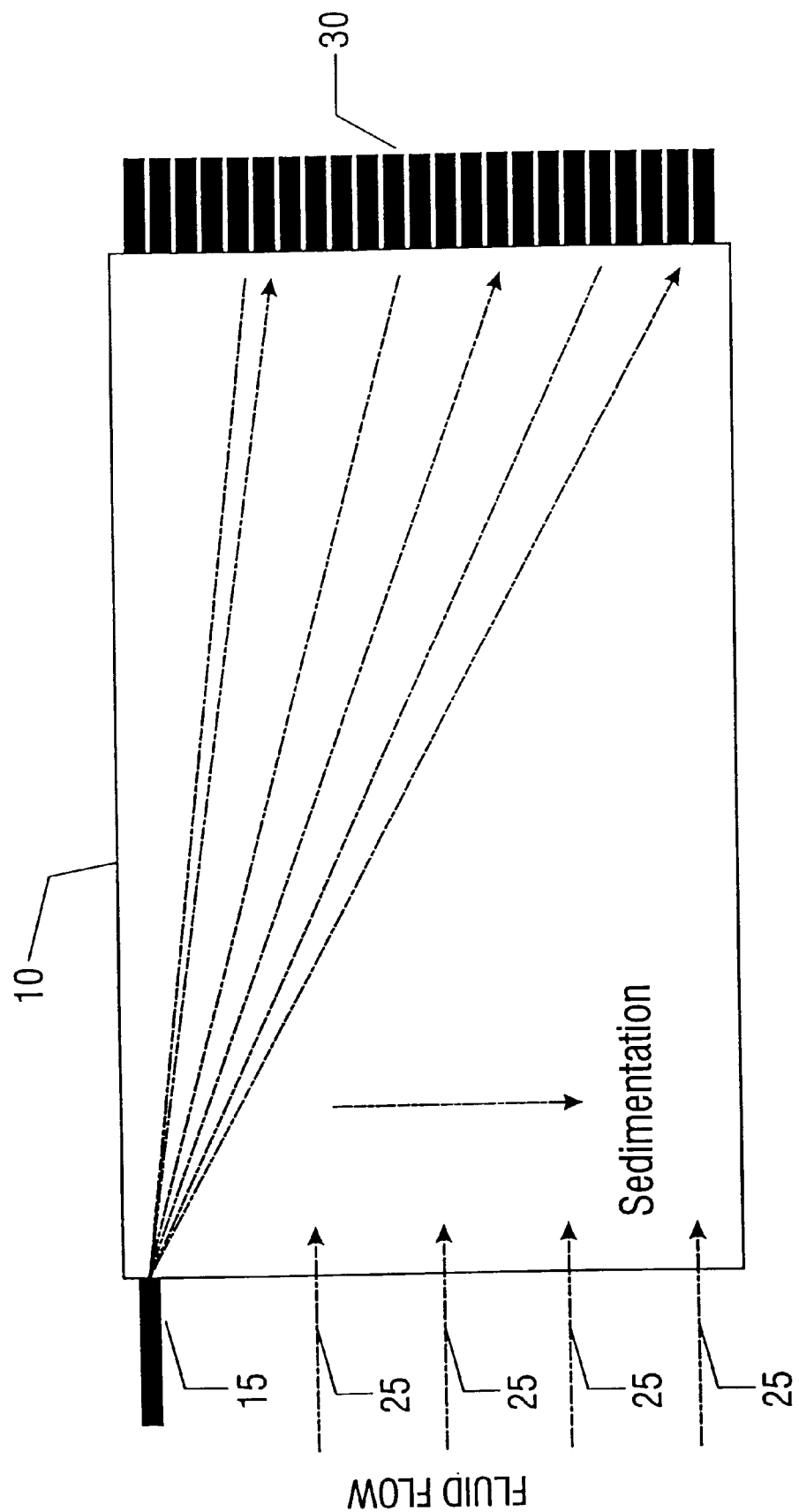
Figure 2B:
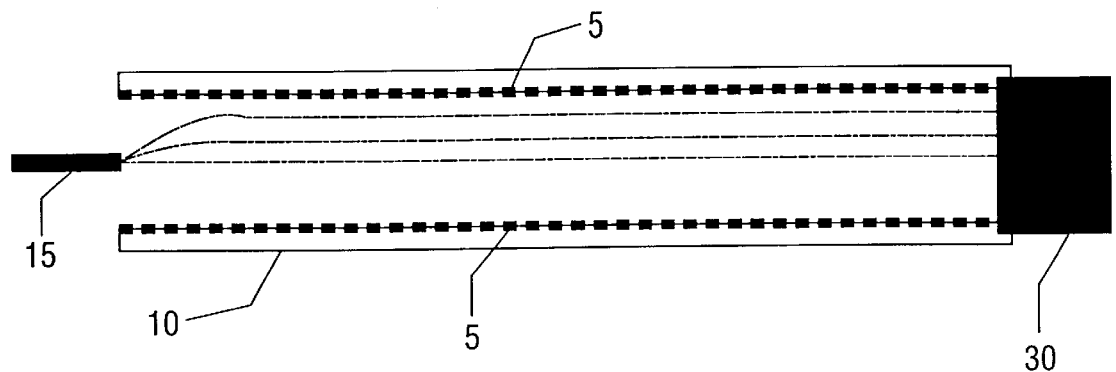

FIG. 2B is a top view of the apparatus of FIG. 2A which describes a typical trajectory of matter introduced into the apparatus.

Figure 2C:
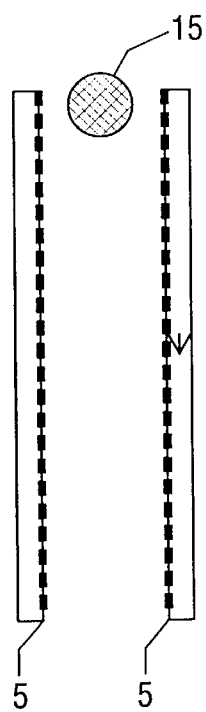

FIG. 2C is an end view of the apparatus of PIG. 2A.

Figure 3A:
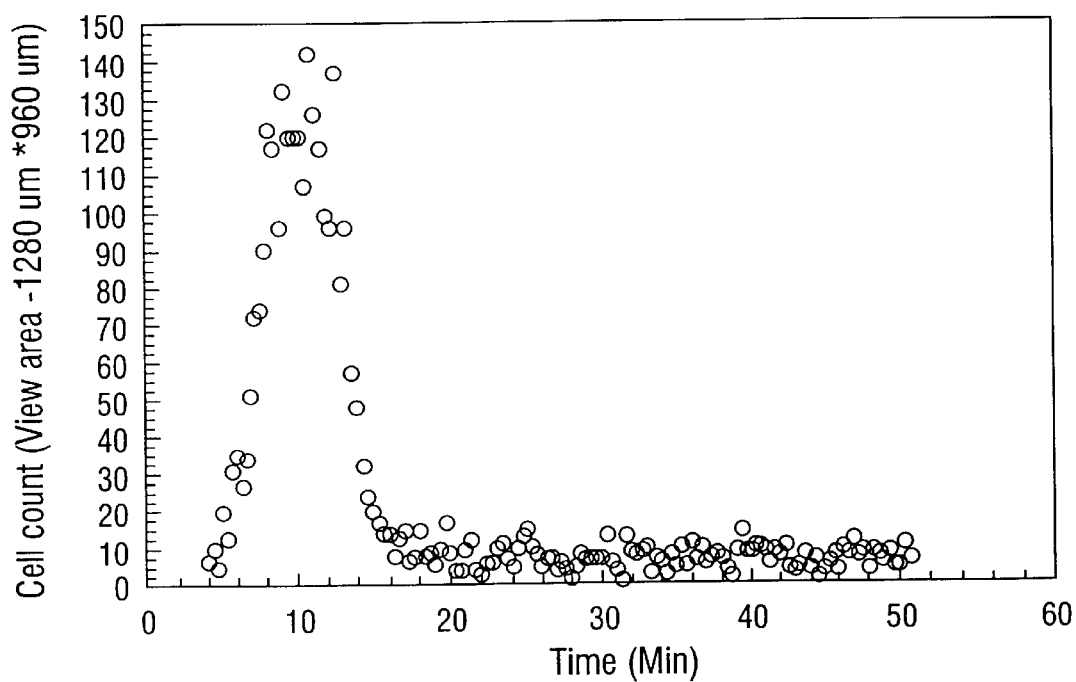

FIG. 3A is a graphical representation of HL-60 cells exiting an apparatus according to the present invention under the influence of field flow fractionation, as a function of time.

Figure 3B:
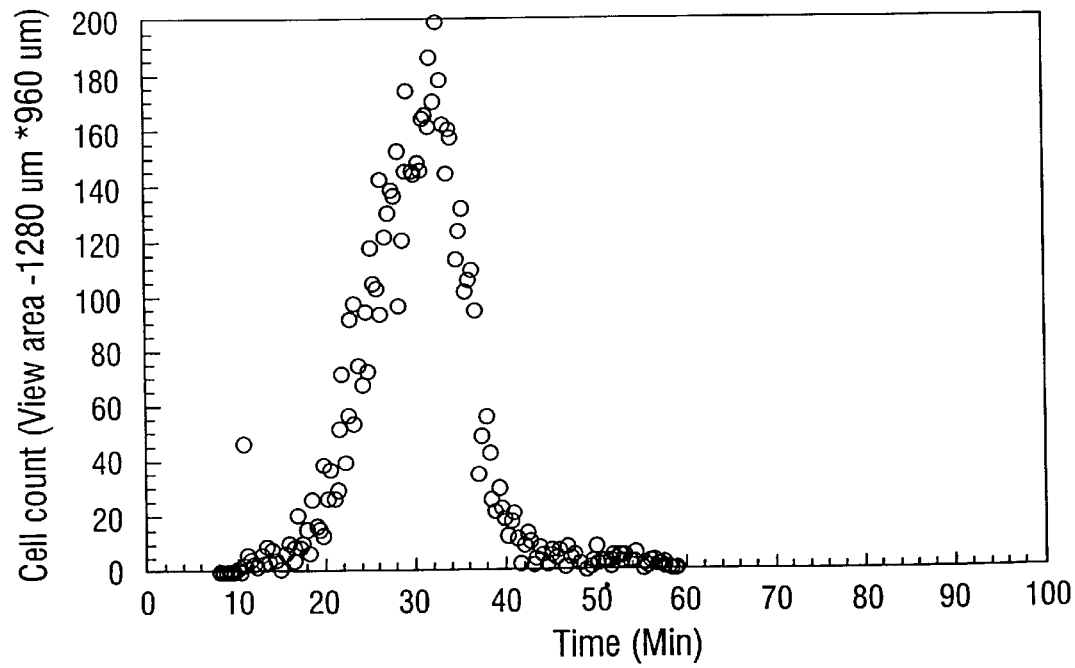

FIG. 3B is a graphical representation of HL-60 cells exiting an apparatus according to the present invention under the influence of field flow fractionation, as a function of time.

Figure 3C:
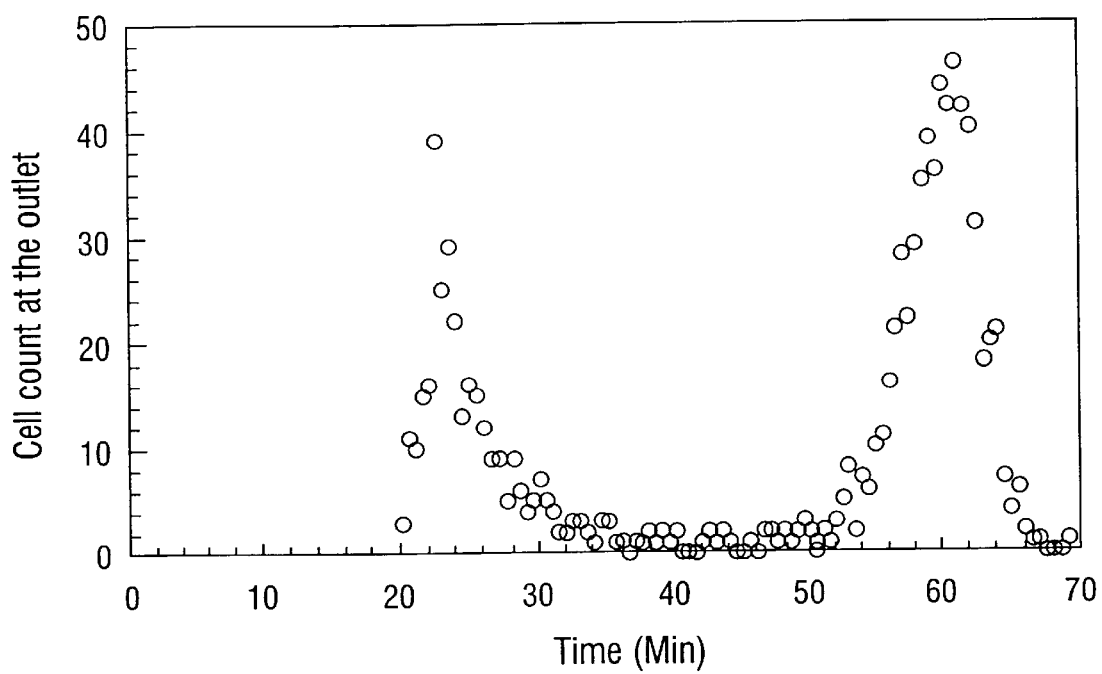

FIG. 3C is a graphical representation of HL-60/Human Whole Blood cells exiting an apparatus according to the present invention under the influence of field flow fractionation, as a function of time.

Figure 4A:
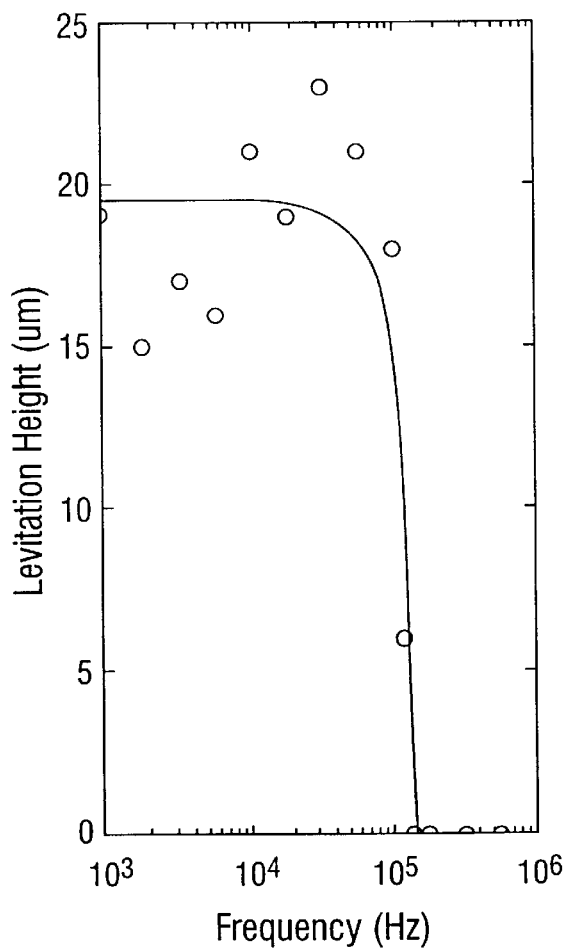

FIG. 4A is a graphical representation of DS19 cell levitation height under the influence of cDEP as a function of frequency.

Figure 4B:
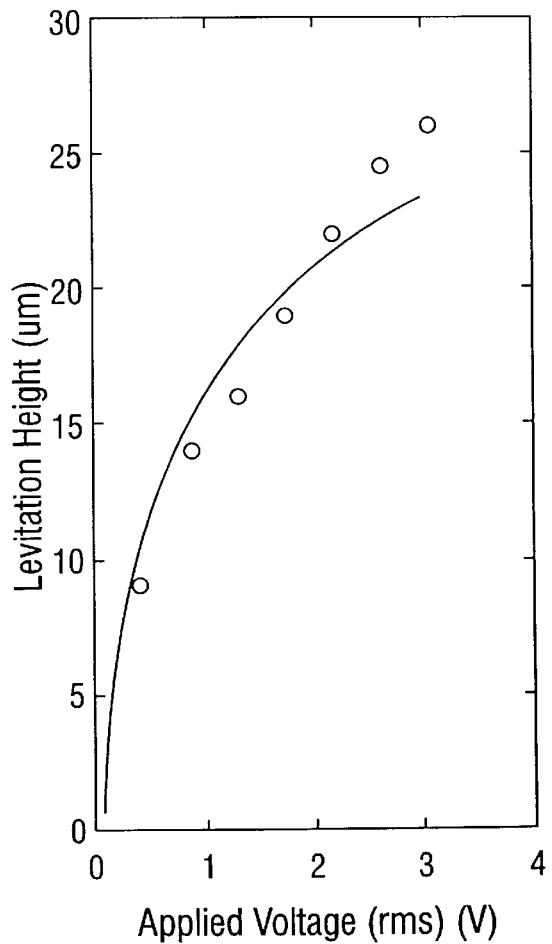

FIG. 4B is a graphical representation of DS 19 cell levitation height under the influence of cDEP as a function of voltage.

Figure 5A:
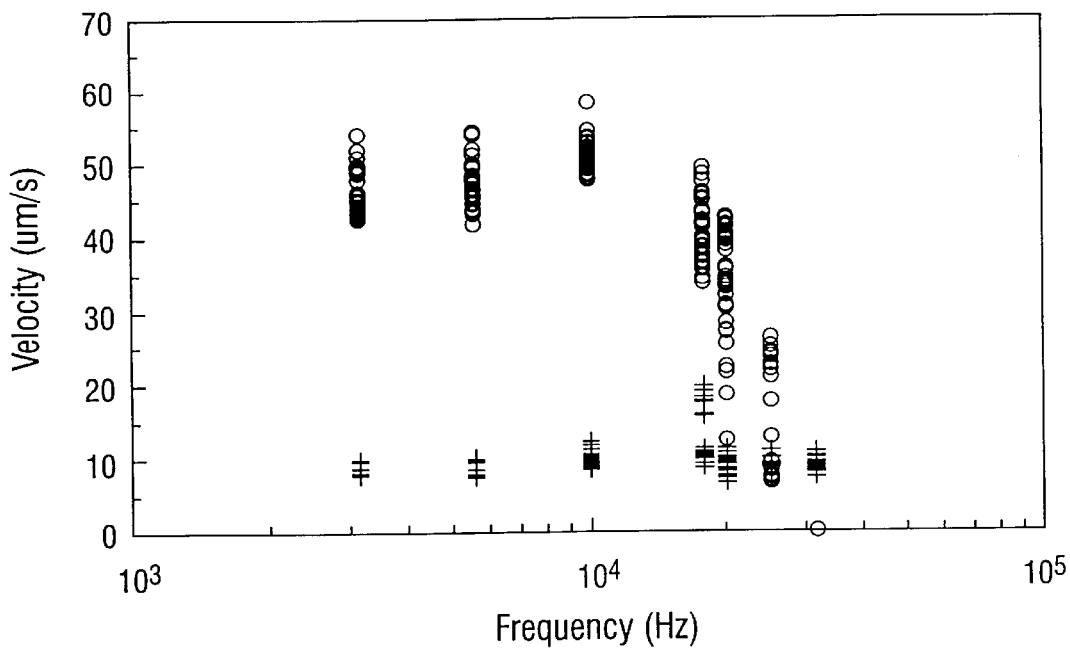

FIG. 5A is a graphical representation of velocity of HL-60 cells travelling through an apparatus according to the present invention under the influence of combined cDEP/FFF forces as a function of frequency.

Figure 5B:
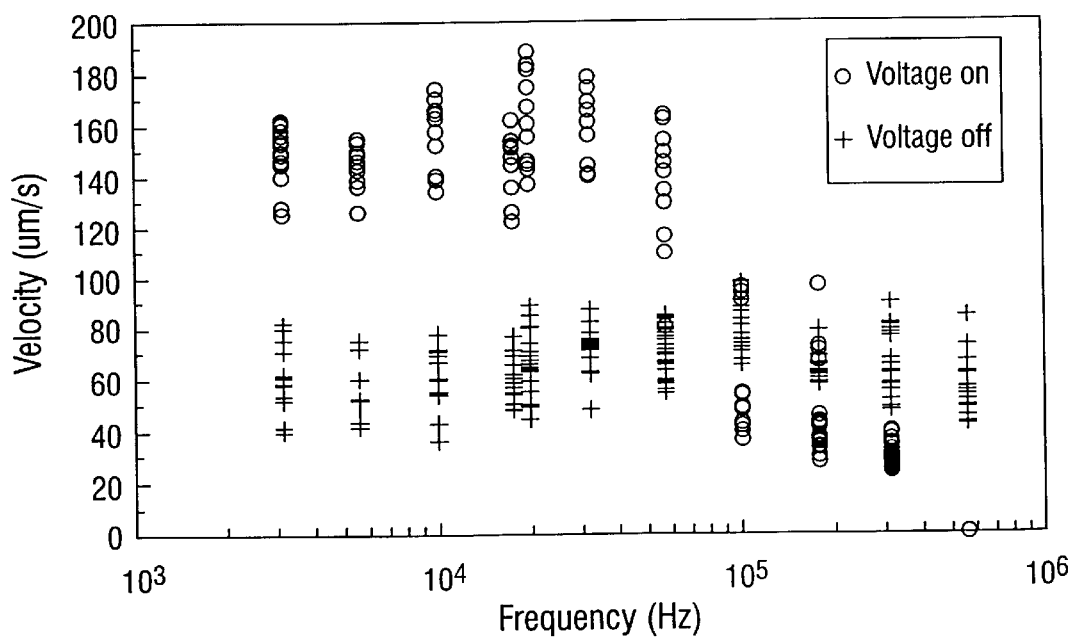

FIG. 5B is a graphical representation of velocity of MDA 468 cells travelling through an apparatus according to the present invention under the influence of combined cDEP/FFF forces as a function of frequency.

Figure 5C:
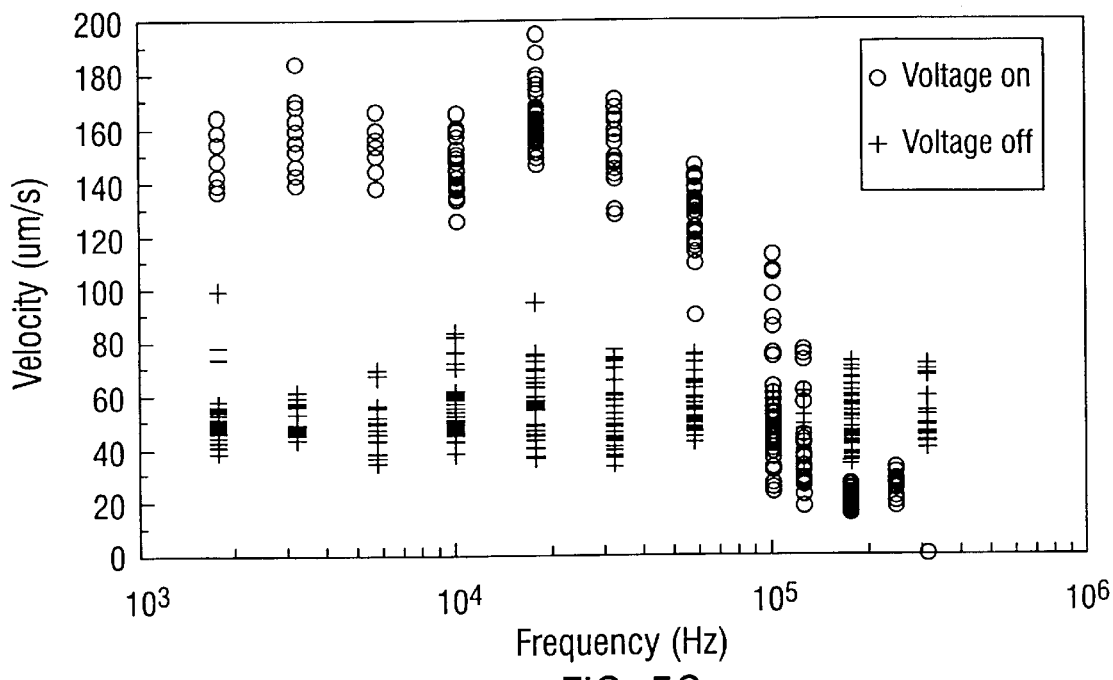

FIG. 5C is a graphical representation of velocity of MDA 435 cells travelling through an apparatus according to the present invention under the influence of combined cDEP/FFF forces as a function of frequency.

Figure 5D:
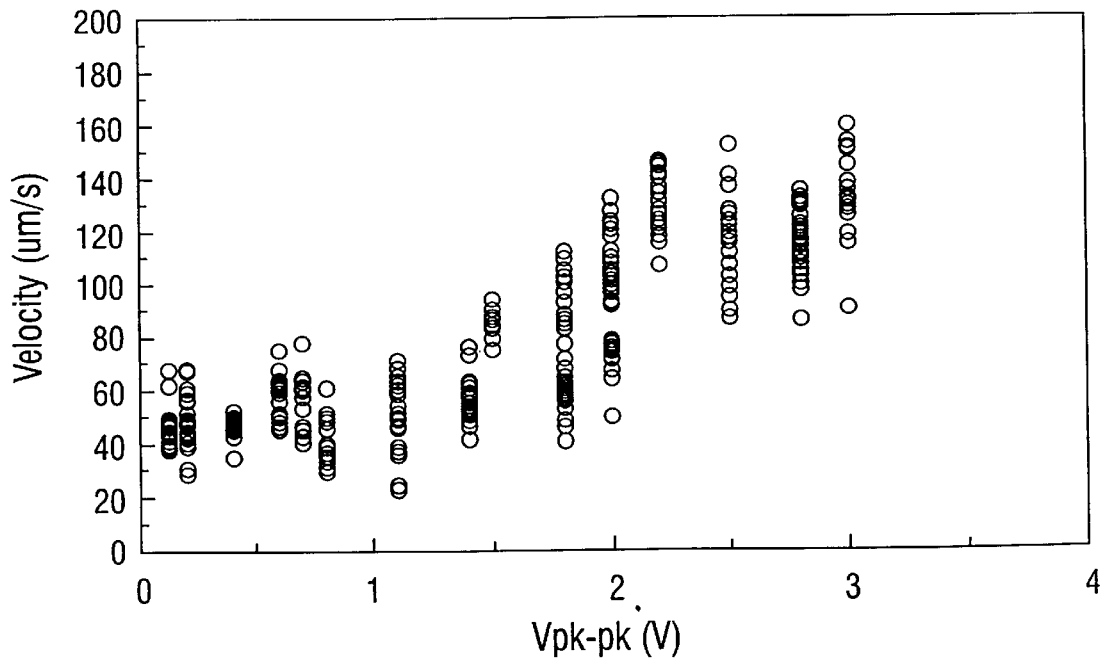

FIG. 5D is a graphical representation of velocity of MDA 435 cells travelling through an apparatus according to the present invention under the influence of combined cDEP/FFF forces as a function of voltage.

DESCRIPTION OF ILLUSTRATIVE EMBODIMENTS

The following examples are included to demonstrate illustrative embodiments of the invention. It should be appreciated by those of skill in the art that the apparatus and techniques disclosed in the examples which follow represent devices and techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. While the following examples use the term particle, the skilled artisan will realize that the present apparatus and methods are suitable to solubilized matter as well.

EXAMPLE I

FIG. 1A shows one exemplary embodiment of an apparatus according to the present invention. In this figure, the electrode array 5 is placed on the bottom of a chamber 10; however it is contemplated that the electrode array may be placed on the top and/or bottom walls and/or side walls of a chamber constructed in accordance with the present invention. As shown in FIG. 1B, the electrode array 5 may be placed along a chamber wall in a position normal to a flow of fluid 35 through the chamber 10. It is to be noted that the array may be adapted at any angle with respect to the fluid flow, for example, parallel or at any other angle. In this embodiment, the walls are aligned to create a thin chamber. The walls are spaced apart by a spacer 20, which may be, for example, constructed of the same material as the chamber walls, or a TEFLON spacer, a sealing compound, or any other dielectric or conductive material. Electrical signals applied to the electrode array create an inhomogeneous alternating electric field that varies with the frequency and magnitude of the input signal. In a particular embodiment, the electrode element 5 may be adapted to be substantially normal to the fluid flow 35, as shown in FIG. 1B. Further electric conductors, which may be electrode buses 40 and 45 may provide electrical signals to alternate elements of electrode array 5. The strength of the electric field is dependent on the applied voltage, position within the chamber, and the size and spacing of electrode elements. For manipulation of mammalian cells, the field strength may be on the order of approximately $1 \times 10^6$ V/m, although this may be much higher for matter placed in an oil medium. The particulate matter desired to be discriminated is introduced into the chamber in a carrier medium that flows into at least one inlet port 15. There may be more than one inlet port however, which permits input of the carrier medium. The carrier medium may be input by a digital syringe pump, a manual syringe, a peristaltic pump, a gravity feed catheter, or the like. As discussed above, the particulate matter may include, for example, biological molecules and non-biological molecules. Also, the matter may include solubilized matter. The carrier medium may be, for example, an eluate consisting of a cell-free suspension buffer, including a mixture of sucrose and dextrose, tissue culture medium, non-ionic or zwitter ionic solutes, or other suspension mediums or non-biological oils, solvents such as phenol alcohol, $CCl_4$, ethylene glycol, or others known in the art.

Alternately, one or more ducts 25 may be provided to input a fluid which may be flowed through chamber 10.

The carrier medium is caused to flow through the chamber and thereby create a laminar flow profile in which the fluid flow rate increases with increasing distance from the chamber top and bottom walls, and reaches its maximum at the center. However, by adjusting the shape of the chamber, for example, a flow profile may be created in which the maximum is at a location other than the center of the chamber. In an exemplary embodiment, this flow rate may be on the order of about 0.1 $\mu$l/min. to about 100 $\mu$l/min., and more preferably about 1 $\mu$l/min. to about 100 $\mu$l/min. Ile electric field applied to the electrode elements 5 creates conventional dieecophoretic forces on the particles in accordance with their dielectric and conductive properties as well as those of the carrier medium.

By controlling the frequency and/or intensity of the applied electric field, the component of the dielectrophoretic force that is normal to the direction of the carrier medium is controlled so as to cause the particles to equilibrate at characteristic distances from the electrode element 5 creating the electric field. In particular embodiments, the dielectrophoretic force may act solely in a vertical direction so as to cause the particles to equilibrate at levitation heights above the chamber bottom wall. Such a force may be present in a vertical chamber or a chamber adapted for use in space. This dielectrophoretic force operates in conjunction with the action of the combined hydrodynamic and gravitational forces. Since the dielectrophoretic force acting on each individual particle depends upon its dielectric permittivity and electrical conductivity at the applied frequency, as well as upon its volume, particles having different properties will be positioned at different distances from the electrode element creating the electric field. Because the fluid at different heights above the chamber bottom wall flows at different velocities, particles having differing physical properties will travel through the chamber 10 at different speeds and emerge at an outlet port 30 at different times. It is to be understood that there may be more than one outlet port from which to collect the particulate matter which exits the chamber 10.

The chamber 10 of FIG. 1A may also utilize twDEP forces in addition to cDEP forces and field flow fractionation, thereby displacing matter in two-dimensions (time and horizontal). In this embodiment, however, the electrode array may be adapted to be substantially parallel to the fluid flow, as shown in FIG. 1C. As discussed above, the cDEP force on the matter causes it to be displaced to a position within the fluid flow. In addition, when the electrode elements 5 are energized with different phases, a twDEP force on matter which acts substantially parallel to the plane of the electrode elements 5, and substantially transverse to the fluid-flow occurs. a Therefore, matter is deflected laterally across the chamber 10 from the original narrow flow stream in which it entered the chamber 10. The deflected matter therefore travels through the chamber 10 and exits through the outlet port 30 at positions laterally displaced from the inlet port 15 through with it entered. Thus, the combined influence of the cDEP and twDEP forces in this embodiment results in a time and horizontal displacement of matter.

EXAMPLE 2

FIG. 2A shows a second embodiment of an apparatus according to the present invention that includes a chamber 10 having two facing electrode arrays 5, as shown in FIGS. 2B and 2C, on opposite surfaces of the chamber. The chamber is turned so that the electrode planes 5 stand substantially vertical. In this embodiment, the chamber is arranged so that the thin sides of the chamber are vertically arranged. It is understood, however, that the electrode planes need not be only vertical, and the present invention contemplates adapting the apparatus at varying angles. Different electrical signals (frequency and magnitude) are applied to the facing electrodes from the signal generator so that particles experience different cDEP forces from the field produced by each array 5. Further, within each facing electrode array 5, different electrical signals may be provided by the signal generator to create an inhomogeneous alternating electric field.

This alternate apparatus may have, for example, one inlet port 15 adapted to receive the particulate matter to be discriminated. The inlet port 15 may be located, for example, close to the top of one end of the chamber 10. This apparatus may also include one or more ducts 25 to introduce a fluid that travels through the chamber 10. The ducts 25, which may be arranged substantially along the entire width of the input end of the chamber 10, serve to introduce a sheet of fluid that travels throughout the chamber 10 in a substantially linear direction.

The introduced fluid carries the particulate matter through the chamber 10. This fluid may be, for example an eluate, such as a cell-free suspension having a mixture of dextrose and sucrose, tissue culture medium, non-ionic or zwitterionic solutions, or other suspension mediums or non-biological oils, solvents such as phenol, alcohol, $CCl_4$, ethylene glycol, or others known in the art. Following transit through the chamber 10, fluid leaves at the opposite end through an exit port. This exit end of the chamber 10 may include, for example, one or more exit ports 30, which may be arranged in one or more arrays of ports as shown in FIG. 2A. In the absence of an applied field, that is, when no electrical signal is applied to the electrode elements 5, particles move through the chamber 10 under the influence of fluid flow. This fluid can be controlled to flow at different speeds. Further, based on the geometrical design of the chamber 10, the fluid may exhibit, for example, a laminar flow, in which the speed of the flow is fastest towards the center of the chamber 10. That is, the hydrodynamic flow profile is along a horizontal plane. Simultaneous to the influence of the fluid flow, the particles undergo sedimentation due to gravitational forces on the particles, so that they exit the chamber 10 at characteristic heights determined by their sedimentation rates.

When electrical signals are applied, however, the particles experience cDEP forces that cause them to move to characteristic distances, known as an equilibrium position, from the side walls of the chamber 10 where the electrode arrays 5 are arranged. In this embodiment, different electrical signals (frequency or magnitude or both) are applied to electrode elements 5 on each of the side walls. Different particles equilibrate at different characteristic distances from the side walls of the chamber, based on the synergism of the differing electrical signals, which create an inhomogeneous electric field, causing DEP forces on the particles. These different signals cause different particles to equilibrate at different characteristic distances from the side walls of the chamber, based on the synergism of the DEP forces caused by the electric field created by the differing signals.

Such particle equilibration depends on the dielectric and conductive properties of the particles, the magnitude and frequency of the electrical fields applied to the electrodes on the facing chamber walls, and the fluid density, viscosity and flow rate as shown in FIG. 2B. Matter introduced into chamber 10 travels at different positions from electrode arrays 5. The velocities of the different particles within the fluid are controlled by the velocity profile of the fluid. Because fluid flowing through a thin chamber sets up a velocity profile, particles that have equilibrated at different distances from the chamber walls will be carried at different velocities and therefore take varying amounts of time to traverse the chamber. The fluid flows at a maximum rate towards the center of the chamber, with this rate proportionately diminishing as distance to the side walls decreases. The fluid flow rate may be between about 0.1 $\mu$l/min. and about 1000 $\mu$l/min., and more preferably between about 1 $\mu$l/min. and about 100 $\mu$l/min. The skilled artisan will recognize, however that variations in the dimensions of the apparatus will affect the fluid flow rate, and that the indicated flow rates are illustrative for the dimensions of the present apparatus.

The distance that particles sediment during their passage across the chamber will depend upon their transit time, as gravity forces act on the particles during their transit through the chamber. Consequently different particles will sediment to different depths based upon the particle's transit time through the chamber 10. Particle sedimentation also depends on particle characteristics, such as size, mass, and volume, for example. Therefore, the time required for particles to travel across the entire length of the chamber is controlled by the fluid flow profile. The placement of particles within the fluid flow profile is in turn determined by the synergism of the differing electrical signals. Discrimination may be accomplished either in "batch mode" or in "continuous mode." In batch mode, an aliquot of particles is injected and collected with respect to the time of transit for the particles and the height of exit at the outlet ports 30. In continuous mode, a constant stream of particles is injected into the inlet port, and particles emerging at different heights are continuously collected.

In an apparatus according to the present invention, it is possible to vary the carrier fluid characteristics at different heights with respect not only to flow rate but also to fluid density, dielectric permittivity, pH and conductivity. In this way additional particle characteristics may be exploited for particular separation applications.

In the general case, the device may be oriented at any angle to take advantage of discriminating aspects of the horizontal and vertical cases described above. In this generalized situation the particle density, sedimentation rate and dielectric properties, together with all components of the cDEP force are utilized. Separation in continuous or batch mode is possible.

Different embodiments of an apparatus according to the present invention may have additional components connected to the outlet ports 30. For example, particles emerging from the exit ports 30 of the apparatus of the present invention may be collected by one or more fraction collectors, or the like. Additionally, the matter may be measured by one or more measuring or characterizing structures, such as a cytometer, for example. Furthermore, when necessary, particles may be transferred to collection wells containing appropriate solutions or media, such as neutral salt buffers, tissue culture media, sucrose solutions, lysing buffers, solvents, fixatives and the like to trap cells exiting the chamber.

An alternate method of operation of this second embodiment utilizes the twDEP force, which acts in a substantially vertical direction from the combined fields produced by the electrode arrays 5. Different electrical signals (frequency, magnitude, and phase, or a combination thereof) may be applied to the facing el codes 5 from the signal generator so that particles experience different cDEP and/or twDEP forces. The cDEP forces may act to displace matter to or away from the electrode plane and thereby equilibrate at an equilibrium position in the fluid flow stream. Matter also sediments as it travels through chamber 10. The distance that matter sediments as it travels depends on the time required to traverse chamber 10 and the sedimentation rate of the matter.

In this alternate method, the distance of matter sedimentation is also affected by the twDEP force. Specifically, the twDEP force acts in a substantially vertical direction when electrode arrays 5 are located on the side walls of chamber 10 and arranged substantially parallel to the fluid flow. Therefore the twDEP force component adds to or opposes the sedimentation forces acting on the matter. Thus the net vertical displacement which the matter experiences as it traverses chamber 10 is modified.

Discrimination in this alternate method may be accomplished in a continuous mode, whereby a constant stream of matter is injected into the inlet ports, and matter emerging at differing vertical displacements is continuously collected at the outlet ports. It may be possible to operate this embodiment in the pulse mode. To further achieve the benefits of discrimintion, it may be possible to vary the carrier fluid characteristics at different vertical displacements by varying flow rate, fluid density, viscosity, dielectric permittivity, pH and conductivity of the carrier fluid. In this way, additional matter characteristics may be exploited for particular discrimination applications.

Methods of Operation

The following descriptions detail construction of an apparatus and methods of operation according to the present invention.

In one embodiment, an apparatus according to the present invention was constructed using two glass slides (1"×1.5", for example) as chamber walls. These walls may be spaced by Teflon spacers; however other methods of separating chamber walls, such as glue, polymer gaskets, or mechanical precision clamps may be used, for example. The distance of separation between walls may be between about 0.1 microns and about 1000 microns, and more preferably between about 10 microns and about 200 microns. In studies using the present apparatus, the distance of separation was 127 microns. One wall of the chamber supported a microelectrode array consisting of about 20 micron wide parallel electrode elements spaced about 20 microns apart. The electrode elements may run along the entire length of the chamber from the input port to the output port. It is understood that the length, width, thickness and spacing of electrode arrays may be altered to create electric fields of differing intensities and different inhomogeneity. It is also to be understood that an array of electrodes may be used with the present invention, or a single electrode element may be sufficient for certain applications, if combined with a ground plane. Further, it is to be understood that the electrode array may not be parallel, and other geometric configurations, such as serially arranged electrodes, linear, polynomial, interleaved, three-dimensional and the like may be utilized.

In an exemplary embodiment, alternate electrode elements may be connected to electrode buses along the two opposite long edges of the chamber wall. These electrode buses are connected to an electrical signal generator, which may be, for example, a function generator. Other suitable signal generators may include, for example, oscillators, pulse generators, digital output cards, klystrons, RF sources, masers, or the like. The electrode array may be fabricated using standard microlithography techniques, as are known in the art. For example, the electrode array may be fabricated by ion beam lithography, ion beam etching, laser ablation, printing, or electrodeposition. The electrode array of the exemplary embodiment described herein consisted of 100 nm gold over a seed layer of 10 nm chromium. It is understood that the present invention contemplates using electrical signals in the range of about 0 to about 15V and about 0.1 kHz to about 180 MHz, and more preferably between about 10 kHz and about 10 MHz. In studies which are described below, the signals were provided by a HP 8116A function generator. The present invention may utilize a fluid flow of about 0.1 $\mu$l/min. to about 500 $\mu$l/min., and more preferably between about 1 $\mu$l/min and about 50 $\mu$l/min. In studies described below, fluid flow in the range of about 1–100 $\mu$l/min, was provided by a digital syringe pump.

Field Flow Fractionation

Cell mixtures in the studies discussed below consisted of blood cells (collected by venipuncture from healthy volunteers and diluted with 90 parts $Ca^{2+}/M^{2+}$-free PBS containing 5 mM hemisodium EDTA) mixed in a ratio of 3:2 with HL-60 leukemia cells that had been cultured under standard conditions and harvested by centrifugation. Cell mixtures were washed twice in isotonic (8.5%) sucrose containing 3 mg/ml dextrose and resuspended at a final concentration of $2\times10^7$ malignant cells and $3\times10^7$ normal blood cells per ml in this same medium. The suspension conductivity was adjusted to 10 mS/m by addition of hemisodium EDTA to a final concentration of approximately 0.7 mM. It is contemplated by the present invention that other methods of obtaining and preparing samples are acceptable. Further, different ratios of the mixture may be used. For example, cell mixtures may be washed twice in an isotonic solution of 8.5% sucrose and 0.3% dextrose, resuspended at a final concentration of $1\times10^7$ malignant cells and $3\times10$ normal blood cells per ml in this same medium, and adjusted to a conductivity of 10 mS/m with a final concentration of ~0.7 mM hemisodium EDTA.

FIG. 3A shows the results of field flow fractionation on a sample of HL-60 cells (ATCC) cultured in a medium of RPMI 1640 10% FBS 22 mM HEPES in an apparatus as described above. The fractionation occurred at a flow rate of 200 $\mu$l/min. As shown in FIG. 3A, a sharp rise in HL-60 cells exiting the apparatus occurs at approximately 10 minutes after the flow of cells began. After this rise, the cell count rapidly tapers to a lower level which continues for approximately 50 minutes. FIG. 3B similarly shows the results of field flow fractionation of HL-60 cells at a flow rate of 100 ul/min. As shown in FIG. 3B, a sharp rise in HL-60 cells exiting the chamber occurs at approximately 30 minutes after the flow of cells began. Again, after this rise, the cell count rapidly tapers to a lower level which continues for approximately 30 minutes.

FIG. 3C shows the results of field flow fractionation on a mixture of HL-60 and human whole blood in a medium of 8.5% sucrose and 3 mg/ml dextrose adjusted to mS/ml, in an apparatus as described above. The fractionation occurred at a flow rate of 100 $\mu$l/min. As shown in FIG. 3C. a sharp rise in the HL-60 cells exiting the chamber occurred at approximately 20 minutes after the flow began. Thereafter, a second rise in the number of cells exiting occurred at approximately 60 minutes, which correlated to the exit of the human blood cells. However, it is noted that cells continue to exit before and after the peaks. Thus, separation by field flow fractionation is not capable of a complete separation. Therefore, FIGS. 3A, 3B, and 3C demonstrate that although field flow fractionation may discriminate and separate some particles of different characteristics, there is needed greater discrimination capabilities.

Three types of studies utilizing the apparatus of the present invention were performed that caused cDEP forces on the particulate matter:

(1) Levitation of Cells Caused by cDEP Force

The levitation of DS-19 murine erythroleukemia cells (M. Rifkind) supported in 8.5% sucrose+0.3% dextrose solution having a conductivity of 56 mS/m was investigated as a function of the frequency and voltage of signals applied to the electrode array in the absence of fluid flow. It is to be understood that various solutions having conductivities in the range of about 10 $\mu$S/m to about 2 S/m, such as tissue culture medium or the like, may be used. Further, it is possible to utilize a collection of cells only. Other solutions may be practicable so long as the conductivity of the solution is either much more conductive or much less conductive than the cell interiors.

The results of this study are shown in FIG. 4A and FIG. 4B. In the frequency range 1 kHz–40 kHz, DS19 cells were levitated to about 20 microns at an applied voltage of 4V peak to peak (p—p), as shown in FIG. 4A. Above 40 kHz, the levitation height dropped rapidly, and when the frequency reached 140 kHz and above, cells were no longer levitated but were instead attracted to electrode edges by positive cDEP.

At an applied frequency of 50 kHz, levitation of DS19 cells occurred when the applied voltage was above about 0.5 V p—p, as shown in FIG. 4B. Above this threshold, the cells levitated and the height of levitation increased with increasing voltage. This behavior was consistent with that predicted by cDEP theory, the dielectric properties of the cells as measured using the technique of electrorotation, and the density of the cells and their supporting medium.

(2) Combined FF/cDEP

A second study using the apparatus discussed above involved the velocity of HL-60 human promyelocytic leukemia cells supported in 8.5% sucrose+0.3% dextrose solution having a conductivity of about 10 mS/m with an established fluid flow in the chamber, as a function of the frequency of the voltage signals applied to the electrode array. When no voltage signal was applied, the cell velocity was about 10 microns per second as they were transported under the influence of an applied fluid flow rate of 10 $\mu$l/min. The fluid flow may be either the solution including the cells to be tested, or it may be another fluid, or the same fluid without the cells. Additionally the solution may be ramped over time to alter, for example, the pH, or conductivity of the solution.

As shown in FIG. SA, addressing the electrodes with voltage signals affected the height at which the cells traveled above the chamber bottom wall and thereby altered their position and velocity in the laminar flow. Below 10 kHz, cell velocity increased to about 50 microns per second with an applied voltage of 3 V p—p. As the frequency was increased in the range of about 10 kHz to about 25 kHz, the cell velocity gradually fell as the levitation height was reduced. Above 30 kHz, these cells were attracted to the electrode and thus they ceased moving. This response with increasing frequency agreed with the behavior expected from the measured electrical properties of the cells.

As shown in FIGS. 5B and 5C, similar results were obtained for studies using other cells having different cell properties. Specifically, FIG. 5B shows the results for MDA 468 cells (kindly supplied by Janet Price) in a solution of 8.5% sucrose 0.3% dextrose conductivity at 10 ms/m at a flow rate of 40 $\mu$l/min at 3 V p—p. FIG. SC shows the results for MDA-435 cells (kindly supplied by Janet Price) in the same solution at a flow rate of 40 µl/min at 3 V p—p. FIG. 5D shows the results for MDA-435 cells at a flow rate of 40 µl/min at a frequency of 31.6 kHz. As noted in FIG. 5D, the velocity of cells increases approximately linearly with voltage.

(3) cDEP/FFF on Mixture of HL-60 and Human Blood Cells

The chambers of the apparatus were preloaded with a mixture of HL-60 and human blood cells in the ratio 1:10 at a total concentration of $5 \times 10^7$ cells/ml. The cells were supported in 8.5% sucrose+0.3% dextrose solution having a conductivity of 10 mS/m. A voltage of 3 V p—p at 40 kHz was applied to the electrodes and fluid flow at the rate of 10 µl/min was started. All of the HL-60 cells were trapped at the edges of the electrode elements, while the human blood cells (mainly erythrocytes) were levitated and were transported by the fluid. By adjusting the frequency in the range of 8–15 kHz, HL-60 cells were also released and their rate of transport controlled relative to the erythrocytes. When HL-60 cells were levitated to heights above or below the erythrocytes, they moved correspondingly more quickly or more slowly than these blood cells depending on their position in the field flow.

The following is an additional study performed according to the present invention. Fluids were injected and removed through slots at each end of the chamber. The outlet port was it furnished with a well to trap cells exiting the chamber. Prior to performing studies, the chamber was soaked for 5 minutes with 20% (w/v) bovine serum albumin solution to render the glass surfaces less adherent to cells. Alternately the glass surfaces may be air blown, or washed and treated with silane. Dielectrophoretic forces were generated by connecting alternate electrodes to sinusoidal voltages of fixed or swept frequencies, and were monitored using an oscilloscope. Forces to remove cells from the separation chamber were provided by laminar flow of an eluate buffer, controlled by two digital syringe pumps connected in push-pull configuration between the inlet and outlet ports of the chamber. A bubble-free path of fluid was maintained between the pumps at all times.

Following injection of approximately 30 µl of the cell mixture (about $1.2 \times 10^6$ cells) to half fill the chamber, a 200 kHz signal of 5 V peak-peak was applied to the electrode array for 30 sec to collect all cells by positive DEP at the high-field regions of the electrode tips. It is not required, however, to only half-fill the chamber, and a larger chamber may allow for better discrimination. Flow of eluate (consisting of cell-free suspension buffer, which may also be a mixture of 8.5% sucrose plus 3 mg/ml dextrose having a conductivity of 10 mS/m), was then started at 5 µl/min. This flow may be accomplished under the control of two digital syringe pumps operating in a push-pull configuration between the inlet and outlet ports of the chamber. Alternately, the flow may be controlled by a peristaltic pump, gravity flow, blood pressure, or the like. The frequency of the applied electric signal was lowered until the tumor cells were selectively retained while the blood cells were eluted and trapped in the collection well. After 20 minutes, cells were removed from the well by cross-flow between two additional syringe ports without disturbing the tumor cells still on the electrodes. The voltage was then turned off to release the cells held by DEP and these were eluted and collected separately.

In a further embodiment, an apparatus according to the present invention was constructed using two glass slides (1"×3", for example) as chamber walls. These walls were spaced apart by TEFLON spacers with a distance of separation of approximately 50 microns. The apparatus may be arranged so that the glass slides comprise the side walls, and the spacers the top and bottom walls. Alternately, the apparatus may be arranged so that the glass slides comprise the is top and bottom walls, and the spacers comprise the side walls. In this exemplary embodiment, the top and bottom walls supported microelectrode arrays consisting of about 20 micron wide parallel electrode elements spaced about 20 microns apart. The electrode arrays may be configured so that the electrode elements on one wall align with the spaces between electrode elements on the other electrode array. The electrode arrays may be further configured so that the electrode elements are arranged along the long walls of the chamber side walls so that the electrodes are aligned substantially parallel to the fluid flow. It is understood that the length, width, thickness and spacing of electrode arrays may be altered to create electric fields of differing intensities and different inhomogeneity, and traveling spatially as a function of varying phase. However, it is also to be understood that the electrode arrays need not be parallel, and other geometric configurations, such as serially arranged electrodes, linear, polynomial, interleaved, three-dimensional and the like may be utilized.

In an exemplary embodiment, alternate electrode elements may be connected to electrode buses along the short ends of the chamber side walls. The electrode buses on one chamber aide wall may receive electrical signals having 0° and 180° relative phase, and the buses on the other chamber side wall may receive signals having 90° and 270° relative phase. It is understood that alternate electrode elements may receive signals having relative phases of differing values. These electrode buses are connected to an electrical signal generator, which may be, for example, a digital synthesizer. Other suitable signal generators may include, but not be limited to, oscillators, function generators, pulse generators, digital output cards, klystrons, RF sources, masers, or the like. The electrode array of the embodiment described herein consisted of 100 nm gold over a seed layer of 10 nm chromium fabricated by standard microlithographic techniques. It is understood that the present invention contemplates using electrical signals in the range of about 0 to about 15V and about 0.1 kHz to about 180 MHz, and more preferably between about 10 kHz and about 10 MHz. In the study described below utilizing this apparatus, the signals were provided by a custom-built digital synthesizer. The present invention may utilize a fluid flow of about 0.1 µl/min. to about 500 µl/min., and more preferably between about 1 µl/min and about 50 µl/min. In studies described below, fluid flow in the range of about 1–100 µl/min, was provided by a digital syringe pump.

(1) Levitation of Cells Caused by gDEP Force

The levitation of DS-19 murine erythroleukemnia cells (M. Rifkind) supported in 8.5% sucrose+0.3% dextrose solution having a conductivity of 10 mS/m was investigated as a function of the frequency of signals applied to the electrode array both in the absence of fluid flow and with a fluid-flow. It is to be understood that various solutions having conductivities in the rage of about 10 µS/m to about 2 S/m, such as tissue culture medium or the like, may be used. Further, it is possible to utilize a collection of cells only. Other solutions may be practicable so long as the conductivity of the solution is either much more conductive or much less conductive than the cell interiors.

The DS19 cell mixed in the suspension medium was introduced into the chamber at a flow rate of 10 µl/min. As the frequency of the electrical signals was gradually increased from approximately 1 kHz to approximately 15 MHz at 3 volts peak-to-peak, three kinetic effects were observed:

(i) 1 to 30 kHz. Cells were levitated above the electrode plane by cDEP forces (typically by about 18 μm, depending on frequency) and moved counter to the applied travelling wave by twDEP forces at rates that increased with increasing frequency to approximately 40 microns/sec. Fast-moving cells overtook slow ones without forming pearl-chains commonly observed when cDEP alone is used for cell manipulation. In the presence of fluid flow applied at right angles to the twDEP forces at a flow rate of 10 μl/min., individual cells were deflected to different degrees depending on their electrical characteristics. Furthermore, the velocity of cells due to the fluid flow depended on their distances from the electrode plane in accordance with cDEP/FFF principles.

(ii) 30 to 50 kHz. The cDEP force acting on the cells was very small and cells remained close to the electrodes at the bottom of the chamber. Some cells were deflected in the same direction as the travelling wave by the twDEP forces, other cells were barely deflected, and some cells were deflected in the opposite direction to the twDEP waves. In the presence of fluid flow at a flow rate of 10 μl/min., maximal differences in cell velocity in the fluid stream occurred due to cDEP/FFF influences, and twDEP forces resulted in different degrees of deflection across the fluid stream for different cells.

(iii) 50 kHz to 15 MHz. Cells were mostly attracted to electrode edges and immobilized under the influence of strongly positive cDEP forces.

These findings agreed with the predictions of generalized dielectrophoresis. They show further that the combined influence of cDEP and twDEP make possible a new type of cell sorting that depends on both the real and imaginary components of the cell electrical polarizability as well as the suspending medium dielectric and conductive properties.

It is contemplated that the apparatus and methods according to the present invention may be used for cell or particle characterization, as a diagnostic tool to identify, for example, cancer cells or other cells that are desired or of interest to the clinician, and as a therapeutic tool to purge a patient sample of undesired cells or other particle.

For example, the methods according to the present invention may be used to characterize the physical properties of an unknown particulate matter. A sample including an unknown biological or organic or mineral sample may be input into the chamber and separated according to the procedures set forth above. Following separation and removal of extraneous particles, the unknown particle may be collected at an output port of the chamber. The particle can then be analyzed using standard particle characterization techniques known in the art, such as those used in diagnostic microbiology and in histology, for example, electron microscopy. After determining characteristics that are unique to a particle, an investigator may then compare these characteristics to the known characteristics of a particle. Therefore, the researcher may determine whether the unknown particle is the same as a known particle, or whether it has similar properties.

In addition, the invention contemplates the characterization of known particles, which may then be used as a reference tool for determining unknown particles based on similar trapping frequencies, voltages, flow rates, and other parameters set forth above. The sample may be introduced into the chamber of the present invention and then be subjected to the separation methods detailed above. By performing these separation techniques, the trapping frequency and release frequency of the particle can be determined. These values are then useful in comparing similar parameters of an unknown sample to this known sample. Certain clinical applications requiring separation of a known particle from an unknown particle would require such values to complete the methods of separation.

A clinical application of the present invention would be to use the present apparatus and methods as a diagnostic tool to screen unknown samples for the presence or absence of various cell types. First, as set forth previously, a patient's sample may be placed in the apparatus, and various cell types may be separated based on previously determined parameters or characteristics. These cells may include cancer cells, or cells infected with bacteria, viruses, protozoans, or parasites, bacteria, viruses protozoans, or they may include cells that are deficient in certain enzymes or cell organelles, altered biopsies, plaques and scrape tests including Pap smears and so forth. Thus, it is well within the scope of the invention to separate all types of particles that have differential sedimentation rates in a fluid stream, based on size, density, dielectric strength, and conductivity, for example. Therefore, the present invention may be used to diagnose the presence of a condition, for example, a cancer, or other cellular disorder.

Another clinical application would be to use the apparatus and methods of the present invention to separate unwanted cells, such as cancerous cells, from a cell population including wanted or normal cells. For example, once a cancer has been detected, for instance in bone marrow, a patient's bone marrow may be input into an apparatus according to the present invention to separate the cancer cells, or preneoplastic cells, from normal cells. These normal cells may then be collected at the output of the chamber and returned to the patient, while the unwanted cancer cells may be later collected at the output of the chamber and characterized, utilized in further studies, or discarded. In this manner, unwanted cells are purged from a normal cell population, while at the same time a particular cell type is enriched, such as tumor cells, normal cells, progenitor cells, etc.

The apparatus and methods disclosed and claimed herein can be made and executed without undue experimentation in light of the present disclosure. While the apparatus and methods of this invention have been described in terms of preferred embodiments, it will be apparent to those of skill in the art that variations may be applied to the apparatus, methods and in the steps or in the sequence of steps of the method described herein without departing from the concept, spirit and scope of the invention. All substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Arnold, W. M. et al. (1982) *Naturwissenischafen,* 69, 297–300.
2. Becker et al. (1995) *Proc. Natl. Acad. Sci.* 92, 860–864.
3. Becker, F. F. et al. (1994) *J. Phys. D: Appl. Phys.* 27(12), 2659–2662.
4. Boyum, A. (1974) *Tissue Antigens* 4, 269–274.
5. Cantrell, D. A. et al. (1992) *Ciba. Found Symp.* 164, 208–222.
6. Chess, L. et al. (1976) in: *In vitro Methods in Cell Mediated and Tumor Immunity,* 255–261.

7. Fischer, A. (1993) *Brit. J. Haematol.* 83, 531–534.
8. Fuhr, G. (1985) Über die rotation dieelektrischer körper in rotierenden feldern, PhD. Dissertation, Humboldt-Universität, Berlin, Chap. 3, 24–53.
9. Gascoyne, P. R. C. et al. (1994) *IEEE. Trans. Ind. Appl.* 30, 829–834.
10. Gascoyne, P. R. C., et al. (1992) *Meas. Sci. Technol.* 3, 439–445.
11. Giddings, J. C., (1993) *Science* 260, 1456–1465.
12. Hagedorn, R. et al. (1992) *Electrophoresis* 13, 49–54.
13. Holzel, R. et al. (1992) *Biochim. Biophyus. Acta* 1101, 195–200.
14. Huang, Y. et al. (1992) *Phys. Med. Biol.* 37, 1499–1517.
15. Huang, Y. et al. (1993) *Phys. Med. Biol.* 37, 1499–1517.
16. Markx, G. H. et al. (1994) *Microbiology* 140, 585–591.
17. Smeland, E. B. et al. (1992) *Leukemia*, 6, 845–852.
18. Smeland et al., (1992) *Leukemia*, 6:845–852.
19. Stout, R. D. (1993) *Curr. Opin. Immunol.* 5(3), 398–403.
20. Wang, X. -B. et al. (1994) *Biochim. Biophys. Acta* 1193, 330–344.
21. Wang, X. -B. et al. (1993) *J. Phys. D: Appl. Phys.* 26, 1278–1285.

What is claimed is:

1. A method for treating a condition in a patient, wherein said condition is indicated by the presence of an identified matter, said method comprising:
    a) obtaining a fluid sample including said identified matter from said patient;
    b) obtaining and disposing horizontally a chamber having at least one inlet port and one outlet port, said chamber having an interior surface and an exterior surface, said chamber further having structural characteristics which cause a transport fluid traveling through said chamber to travel at differing velocities according to a velocity profile; a plurality of electrode elements adapted along a portion of said chamber; at least one duct entering the chamber to carry said transport fluid through the chamber;
    c) introducing said sample of said patient into said at least one inlet port;
    d) introducing the transport fluid into the at least one duct, causing a fluid flow at a flow rate according to said velocity profile within said chamber;
    e) applying at least one electrical signal provided by an electrical signal generator at a holding frequency of said identified matter to said plurality of electrode elements at different phases, wherein said plurality of electrode elements is energized and creates a traveling electric field, thereby causing at least one dielectrophoretic force on said identified matter having components normal to the direction of said fluid flow;
    f) holding said identified matter in close proximity to said plurality of electrode elements;
    g) transporting said sample without said identified matter by said transport fluid at a velocity according to said velocity profile;
    h) collecting said sample without said identified matter at said at least one outlet port; and
    i) returning said sample without said identified matter to said patient to thereby treat said condition.

2. The method of claim 1, wherein said identified matter comprises cancer cells.

3. A method for treating a cancer condition in a patient by separating cancer cells from normal cells utilizing dielectrophoresis and field flow fractionation, said method comprising:
    a) obtaining a suspension or fluid sample containing cancer cells and normal cells from said patient;
    b) obtaining and disposing horizontally a chamber having at least one inlet and one outlet port, said chamber having an interior surface and an exterior surface, said chamber further having structural characteristics which cause a transport fluid traveling through said chamber to travel at differing velocities according to a velocity profile; a plurality of electrode elements adapted along a portion of said chamber; at least one duct entering the chamber to carry said transport fluid through the chamber;
    c) introducing said sample into said at least one inlet port;
    d) introducing the transport fluid into the at least one duct, causing a fluid flow at a flow rate according to said velocity profile within said chamber;
    e) applying at least one electrical signal provided by an electrical signal generator to said plurality of electrode elements at different phases, wherein said plurality of electrode elements is energized and creates a traveling electric field, thereby causing at least one dielectrophoretic force on said cancer cells and said normal cells having components normal to the direction of said fluid flow, thereby displacing said cancer cells from said normal cells; wherein said cancer cells and said normal cells travel through said chamber at said differing velocities according to said cancer cells and said normal cells respective positions within said transport fluid, and said cancer cells and said normal cells exit from said chamber at said at least one outlet port at positions corresponding to said displacement between said cancer cells and said normal cells; and
    returning said normal cells to said patient to thereby treat said cancer condition.

4. A method according to claim 3, wherein said cancer cells and said normal cells exit said at least one outlet port at times proportionate to said differing velocities.

5. A method according to claim 3, wherein said cancer cells and said normal cells exit said at least one outlet port at times proportionate to said cancer cells and said normal cells displacement within said fluid flow.

6. A method for removing preselected matter from a sample containing said preselected matter and non-selected matter, comprising:
    a) obtaining a sample containing a suspension or fluid of preselected matter and non-selected matter;
    b) obtaining a chamber having inlet and outlet ports, said chamber adapted to cause said sample to flow at differing velocities according to a velocity profile; an electrode structure adapted along at least a portion of said chamber;
    c) introducing said sample into said inlet port;
    d) creating a traveling electric field in said chamber to effect a dielectrophoretic force on said sample, said traveling electric field being created at a holding frequency of said preselected matter; said holding frequency causing said preselected matter to be held in close proximity to said electrode structure; and
    e) collecting said sample without said preselected matter at said outlet port.

7. The method of claim 6, wherein said preselected matter comprises cancer cells.

8. The method of claim 6, wherein said sample comprises a blood supply of a patient.

9. The method of claim 6, wherein said sample comprises bone marrow of a patient.

* * * * *